United States Patent
Chavan et al.

(10) Patent No.: US 8,983,617 B2
(45) Date of Patent: *Mar. 17, 2015

(54) METHOD AND APPARATUS FOR CONTROLLING NEUROSTIMULATION ACCORDING TO PHYSICAL STATE

(71) Applicant: Cardiac Pacemakers, Inc., St. Paul, MN (US)

(72) Inventors: Abhi V. Chavan, Maple Grove, MN (US); Keith R. Maile, New Brighton, MN (US); David J. Ternes, Roseville, MN (US); Juan Gabriel Hincapie Ordonez, Maple Grove, MN (US); Stephen Ruble, Lino Lakes, MN (US); Jason J. Hamann, Blaine, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/858,405

(22) Filed: Apr. 8, 2013

(65) Prior Publication Data

US 2013/0226264 A1 Aug. 29, 2013

Related U.S. Application Data

(63) Continuation of application No. 13/272,786, filed on Oct. 13, 2011, now Pat. No. 8,433,419.

(60) Provisional application No. 61/392,767, filed on Oct. 13, 2010.

(51) Int. Cl.
*A61N 1/00* (2006.01)
*A61N 1/36* (2006.01)

(52) U.S. Cl.
CPC ........ *A61N 1/36139* (2013.01); *A61N 1/36135* (2013.01); *A61N 1/36053* (2013.01)
USPC .......................................................... 607/59

(58) Field of Classification Search
CPC .... A61N 1/36; A61N 1/3605; A61N 1/37247
USPC .......................................................... 607/59
See application file for complete search history.

(56) References Cited

U.S. PATENT DOCUMENTS

| 5,725,562 A | 3/1998 | Sheldon |
| 5,957,957 A | 9/1999 | Sheldon |

(Continued)

FOREIGN PATENT DOCUMENTS

EP 0243589 B1 12/1992

OTHER PUBLICATIONS

"U.S. Appl. No. 13/272,786, Notice of Allowance mailed Jan. 2, 2013", 8 pgs.

(Continued)

*Primary Examiner* — George Manuel
(74) *Attorney, Agent, or Firm* — Schwegman Lundberg & Woessner, P.A.

(57) ABSTRACT

A neurostimulation system senses a signal indicative of a patient's physical state such as posture and/or activity level. In various embodiments, a stored value for each of stimulation parameters controlling delivery of neurostimulation is selected according to the patient's physical state. In various embodiments, values of the stimulation parameters are approximately optimized for each of a number of different physical states, and are stored for later selection.

20 Claims, 27 Drawing Sheets

(56) References Cited

U.S. PATENT DOCUMENTS

| | | |
|---|---|---|
| 6,044,297 A | 3/2000 | Sheldon et al. |
| 6,259,948 B1 | 7/2001 | Florio et al. |
| 6,351,672 B1 | 2/2002 | Park et al. |
| 6,466,821 B1 | 10/2002 | Pianca et al. |
| 6,658,292 B2 | 12/2003 | Kroll et al. |
| 6,662,047 B2 | 12/2003 | Sorensen et al. |
| 6,751,503 B1 | 6/2004 | Kroll |
| 6,937,900 B1 | 8/2005 | Pianca et al. |
| 7,123,967 B2 | 10/2006 | Weinberg |
| 7,221,979 B2 | 5/2007 | Zhou et al. |
| 7,330,760 B2 | 2/2008 | Heruth et al. |
| 7,395,113 B2 | 7/2008 | Heruth et al. |
| 7,447,545 B2 | 11/2008 | Heruth et al. |
| 7,471,290 B2 | 12/2008 | Wang |
| 7,491,181 B2 | 2/2009 | Heruth et al. |
| 7,558,627 B1 | 7/2009 | Turcott |
| 7,647,106 B2 | 1/2010 | Virag et al. |
| 7,792,583 B2 | 9/2010 | Miesel et al. |
| 7,805,196 B2 | 9/2010 | Miesel et al. |
| 7,908,013 B2 | 3/2011 | Miesel et al. |
| 7,957,797 B2 | 6/2011 | Bourget et al. |
| 7,957,809 B2 | 6/2011 | Bourget et al. |
| 8,135,473 B2 | 3/2012 | Miesel et al. |
| 8,150,531 B2 | 4/2012 | Skelton |
| 8,190,253 B2 | 5/2012 | Heruth et al. |
| 8,200,340 B2 | 6/2012 | Skelton et al. |
| 8,209,028 B2 | 6/2012 | Skelton et al. |
| 8,219,206 B2 | 7/2012 | Skelton et al. |
| 8,231,555 B2 | 7/2012 | Skelton et al. |
| 8,231,556 B2 | 7/2012 | Skelton et al. |
| 8,280,517 B2 | 10/2012 | Skelton et al. |
| 8,290,596 B2 | 10/2012 | Wei et al. |
| 8,315,710 B2 | 11/2012 | Skelton et al. |
| 8,323,218 B2 | 12/2012 | Davis et al. |
| 8,332,041 B2 | 12/2012 | Skelton et al. |
| 8,388,555 B2 | 3/2013 | Panken et al. |
| 8,396,554 B2 | 3/2013 | Miesel et al. |
| 8,396,565 B2 * | 3/2013 | Singhal et al. ............... 607/116 |
| 2005/0245988 A1 | 11/2005 | Miesel |
| 2007/0118056 A1 | 5/2007 | Wang et al. |
| 2007/0255118 A1 | 11/2007 | Miesel et al. |
| 2007/0299476 A1 | 12/2007 | Park et al. |
| 2008/0021504 A1 | 1/2008 | McCabe et al. |
| 2008/0082001 A1 | 4/2008 | Hatlestad et al. |
| 2008/0234780 A1 | 9/2008 | Smith et al. |
| 2009/0318983 A1 | 12/2009 | Armoundas et al. |
| 2010/0010381 A1 | 1/2010 | Skelton et al. |
| 2010/0015702 A1 | 1/2010 | Rao et al. |
| 2010/0015704 A1 | 1/2010 | Mertsching et al. |
| 2010/0076511 A1 | 3/2010 | Heil, Jr. et al. |
| 2010/0114195 A1 | 5/2010 | Burnes et al. |
| 2012/0016435 A1 * | 1/2012 | Rom ............................ 607/45 |
| 2012/0095530 A1 | 4/2012 | Chavan et al. |

OTHER PUBLICATIONS

Alametsä, J, et al., "Ballistocardiography in sitting and horizontal positions", Physiol Meas.; 29(9), (Sep. 2008), 1071-1087.

Barantke, Melanie, et al., "Effects of Gender and Aging on Differential Autonomic Responses to Orthostatic Maneuvers", Journal of Cardiovascular Electrophysiology 19(12), (Dec. 2008), 1296-1303.

Ishizawa, Tetsuro, et al., "Heart Rate and Blood Pressure Variability and Baroreflex Sensitivity in Patients with Anorexia Nervosa", Psychosomatic Medicine 70(6), (Jul. 2008), 695-700.

Karas, Maria, et al., "Attenuation of Autonomic Nervous System Functions in Hypertensive Patients at Rest and During Orthostatic Stimulation", Journal of Clinical Hypertension 10(2), (Feb. 2008), 97-104.

Williams, Gregory C, et al., "The Impact of Posture on Cardiac Repolarization: More Than Heart Rate?", Journal of Cardiovascular Electrophysiology 17(4), (Apr. 2006), 352-358.

Yang, Jen-Lin, et al., "Comparison of Effect of 5 Recumbent Positions on Autonomic Nervous Modulation in Patients with Coronary Artery disease", Circulation Journal; 72(6), (Jun. 2008), 902-908.

* cited by examiner

METHOD AND APPARATUS FOR CONTROLLING NEUROSTIMULATION ACCORDING TO PHYSICAL STATE

CLAIM OF PRIORITY

This application is a continuation of U.S. patent application Ser. No. 13/272,786, entitled "METHOD AND APPARATUS FOR CONTROLLING NEUROSTIMULATION ACCORDING TO PHYSICAL STATE", filed on Oct. 13, 2011, now issued as U.S. Pat. No. 8,433,419, which claims the benefit of priority under 35 U.S.C. §119(c) of U.S. Provisional Patent Application Ser. No. 61/392,767, entitled "METHOD AND APPARATUS FOR CONTROLLING NEUROSTIMULATION ACCORDING TO PHYSICAL STATE", filed on Oct. 13, 2010, each of which are herein incorporated by reference in its entirety.

TECHNICAL FIELD

This document relates generally to neurostimulation and more particularly to a neurostimulation system that adjusts stimulation parameters according to a patient's physical state such as posture and/or activity level.

BACKGROUND

Autonomic modulation therapy (AMT) such as vagus nerve stimulation has been applied to modulate various physiologic functions and treat various diseases. For example, cardiovascular functions are modulated by neural signals in portions of the autonomic nervous system. The heart is innervated with sympathetic and parasympathetic nerves. Neural activities in these nerves are known to regulate, among other things, heart rate, blood pressure, and myocardial contractility. Modulation of such neural activities by neurostimulation therefore provides for modulation of such cardiovascular functions. One example is the modulation of cardiac functions in a patient suffering heart failure or myocardial infarction. Electrical stimulation applied to the vagus nerve is known to decrease the heart rate and the contractility, lengthening the systolic phase of a cardiac cycle, and shortening the diastolic phase of the cardiac cycle. Such effects of vagus nerve stimulation allow for control of myocardial remodeling. In addition to treating cardiac disorders such as myocardial remodeling, vagus nerve stimulation is also known to be effective in treating disorders including, but not limited to, depression, anorexia nervosa/eating disorders, pancreatic function, epilepsy, hypertension, inflammatory disease, and diabetes.

A patient's physical state, such as posture and activity level, is known to affect the patient's autonomic activities and balance. At least because AMT and the patient's physical state both modulate autonomic activities, there is a need to control AMT with considerations for the physical state.

SUMMARY

A neurostimulation system senses a signal indicative of a patient's physical state such as posture and/or activity level. In various embodiments, a stored value for each of stimulation parameters controlling delivery of neurostimulation is selected according to the patient's physical state. In various embodiments, values of the stimulation parameters are approximately optimized for each of a number of different physical states, and are stored for later selection.

In one embodiment, a system for delivering neurostimulation includes a sensor circuit, a stimulation output circuit, and a stimulation control circuit. The sensor circuit senses a signal indicative of a physical state of a patient and sets a current value for a sensor parameter representing the physical state to one of predefined values of the sensor parameter using the sensed signal. The stimulation output circuit delivers the neurostimulation. The stimulation control circuit controls the delivery of the neurostimulation using a plurality of stimulation parameters including one or more sensor-driven parameters, and includes a storage circuit and a stimulation parameter adjuster. The storage circuit stores one or more values for each parameter of the plurality of stimulation parameters. The one or more values include sensor-dependent values for each sensor-driven parameter of the one or more sensor-driven parameters. The sensor-dependent values each correspond to a value of the predefined values of the sensor parameter. The stimulation parameter adjustor determines whether a stored sensor-dependent value for each parameter of the one or more sensor-driven parameters is currently optimal, and selects the stored sensor-dependent value for the each parameter in response to the determination that the stored sensor-dependent value for the each parameter is currently optimal. The stored sensor-dependent value corresponds to the current value of the sensor parameter.

In one embodiment, a method for controlling neurostimulation is provided. Neurostimulation is delivered to a patient. The delivery of the neurostimulation is controlled using a plurality of stimulation parameters. The plurality of stimulation parameters includes one or more sensor-driven parameters. A signal indicative of a physical state of the patient is sensed. A current value of a sensor parameter is set to a value selected from a plurality of predefined values using the sensed signal. A stored sensor-dependent value is identified for each parameter of the one or more sensor-driven parameters for the current value of the sensor parameter. Whether the identified stored sensor-dependent value is currently optimal is determined. The identified stored sensor-dependent value is applied in the controlling of the delivery of the neurostimulation in response to a determination that the identified stored sensor-dependent value is currently optimal.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof. The scope of the present invention is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description provides examples, and the scope of the present invention is defined by the appended claims and their legal equivalents.

It should be noted that references to "an", "one", or "various" embodiments in this disclosure are not necessarily to the same embodiment, and such references contemplate more than one embodiment.

This document discusses a system and method for delivering neurostimulation to a patient and controlling the delivery of the neurostimulation according to the patient's physical state. Such physical state is known to affect outcome of the neurostimulation. Examples of the physical state include the patient's posture and activity level. In various embodiments, the present system and method provide for monitoring of the patient, titration of neurostimulation, and application of the neurostimulation for each of various predefined physical states. In various embodiments, the present system allows for optimization of dose of neurostimulation for the patient and maximization of battery longevity for an implantable device delivering the neurostimulation.

In this document, a "user" includes a physician or other healthcare professional using the present system and method to treat a patient. While autonomic modulation therapy (AMT) for modulating cardiovascular functions is discussed in this document as a specific example, the present system and method generally apply to any neurostimulation whose result is affected by the patient's physical state such as posture and activity level.

Figure 1:
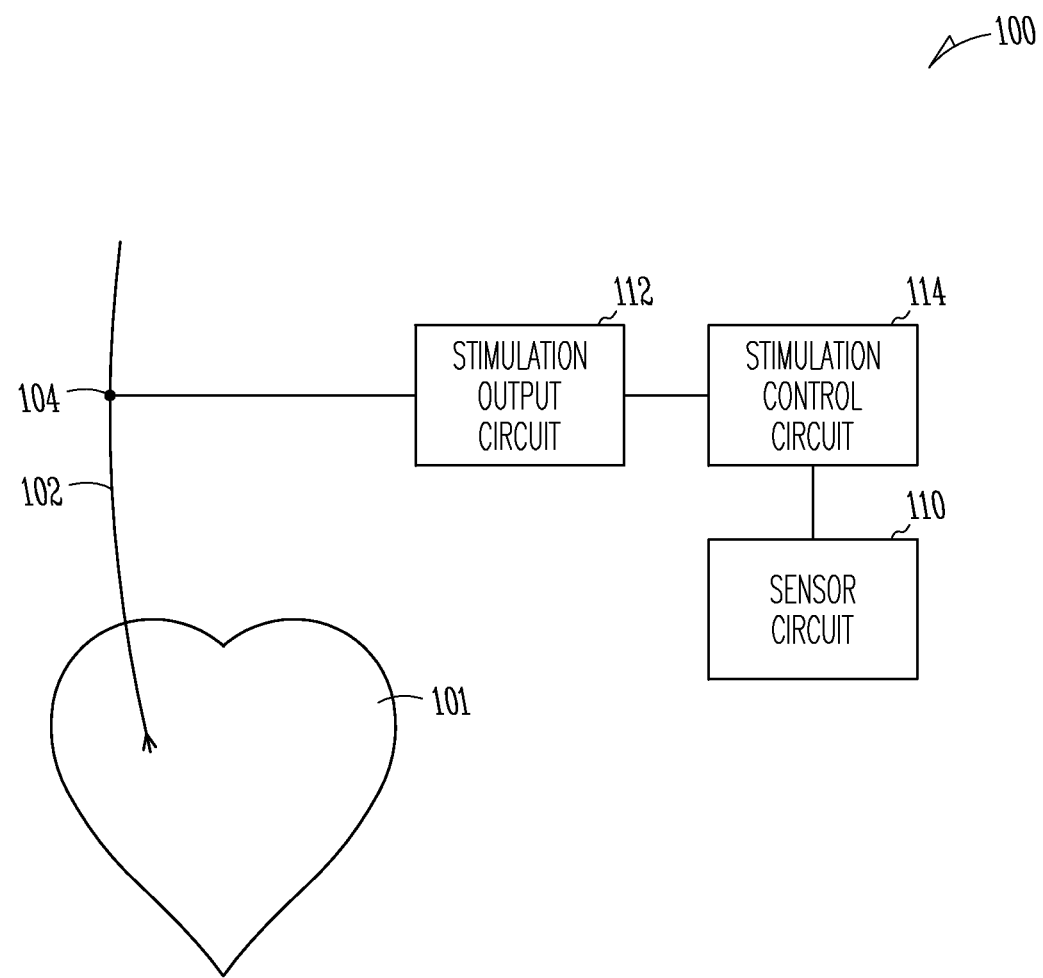
FIG. 1 is an illustration of an embodiment of a neurostimulation system allowing for titration of autonomic modulation therapy (AMT) for a patient's physical state and portions of an environment in which the system is used.

FIG. 1 is an illustration of an embodiment of a neurostimulation system 100 allowing for titration of AMT for a patient's physical state and portions of an environment in which system 100 is used. System 100 includes a stimulation output circuit 112, a stimulation control circuit 114, and a sensor circuit 110. A stimulation electrode 104 is electrically connected to stimulation output circuit 112 and placed on a nerve 102 to allow for delivery of neurostimulation from stimulation output circuit 112 to modulate functions of the patient's heart 101. Nerve 102 represents a nerve of the patient's autonomic nervous system, such as the vagus nerve.

Sensor circuit 110 senses a signal indicative of a physical state of the patient and sets a current value for a sensor parameter representing the physical state to one of predefined values of the sensor parameter using the sensed signal. Examples of the signal and the predefined values are discussed below, with reference to FIG. 4. Stimulation output circuit 112 delivers the neurostimulation. In one embodiment, stimulation output circuit 112 delivers electrical neurostimulation pulses. Stimulation control circuit 114 controls delivery of the neurostimulation from stimulation output circuit 112. In various embodiments, stimulation control circuit 114 controls the delivery of the neurostimulation according to the current value of the sensor parameter. In various embodiments, stimulation parameters used for controlling the neurostimulation are approximately optimized for the predefined values of the sensor parameter. Sensor circuit 110 and stimulation control circuit 114 are further discussed below, with reference to FIGS. 2-5 for example.

In various embodiments, the circuit of system 100, including its various elements discussed in this document, is implemented using a combination of hardware and software. In various embodiments, stimulation control circuit 114 and/or sensor circuit 110, including their various elements discussed in this document, may be implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof.

Figure 2:
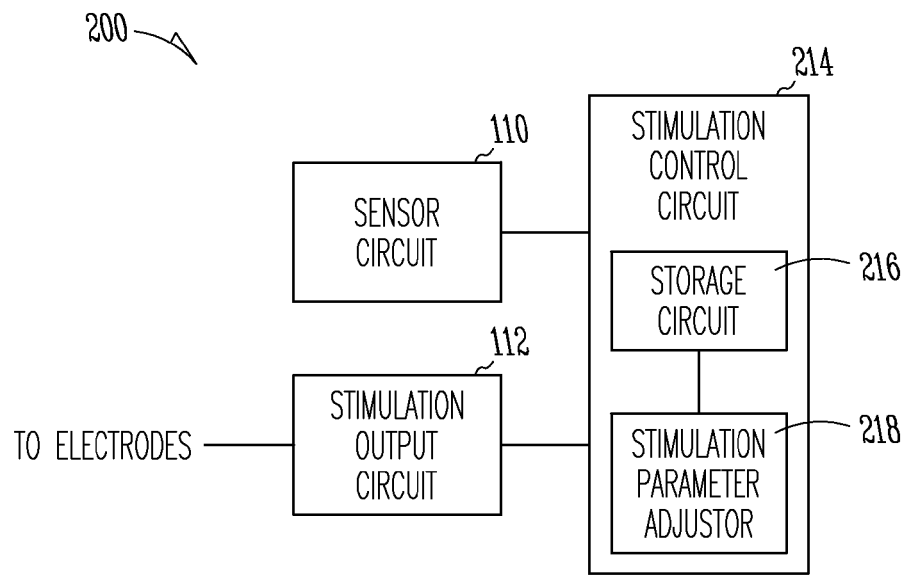
FIG. 2 is a block diagram illustrating an embodiment of the neurostimulation system.

FIG. 2 is a block diagram illustrating an embodiment of a neurostimulation system 200. System 200 represents an embodiment of system 100 and includes sensor circuit 110, stimulation output circuit 112, and a stimulation control circuit 214. System 200 applies the neurostimulation according to the patient's physical state.

Stimulation control circuit 214 controls the delivery of the neurostimulation using a plurality of stimulation parameters including one or more sensor-driven parameters. The one or more sensor-driven parameters each have a value that is adjusted using the sensor parameter. In one embodiment, the neurostimulation is delivered in the form of electrical stimulation pulses, and examples for the stimulation parameters include pulse amplitude, pulse width, pulse frequency or inter-pulse interval, duty cycle, and periodic dose. Stimulation control circuit 214 includes a storage circuit 216 and a stimulation parameter adjustor 218. Storage circuit 216 stores one or more values for each parameter of the plurality of stimulation parameters. The one or more values include sensor-dependent values for each of the one or more sensor-driven parameters. The sensor-dependent values each correspond to one of the predefined values of the sensor parameter. Stimulation parameter adjustor 218 determines whether a stored sensor-dependent value for each parameter of the one or more sensor-driven parameters is currently optimal, and selects the stored sensor-dependent value for the each parameter in response to the determination that the stored sensor-dependent value for the each parameter is currently optimal. The stored sensor-dependent value corresponds to the current value of the sensor parameter. The selected sensor-dependent value is then used by stimulation control circuit 214 to control the delivery of the neurostimulation while the current value of the sensor parameter remains unchanged.

Figure 3:
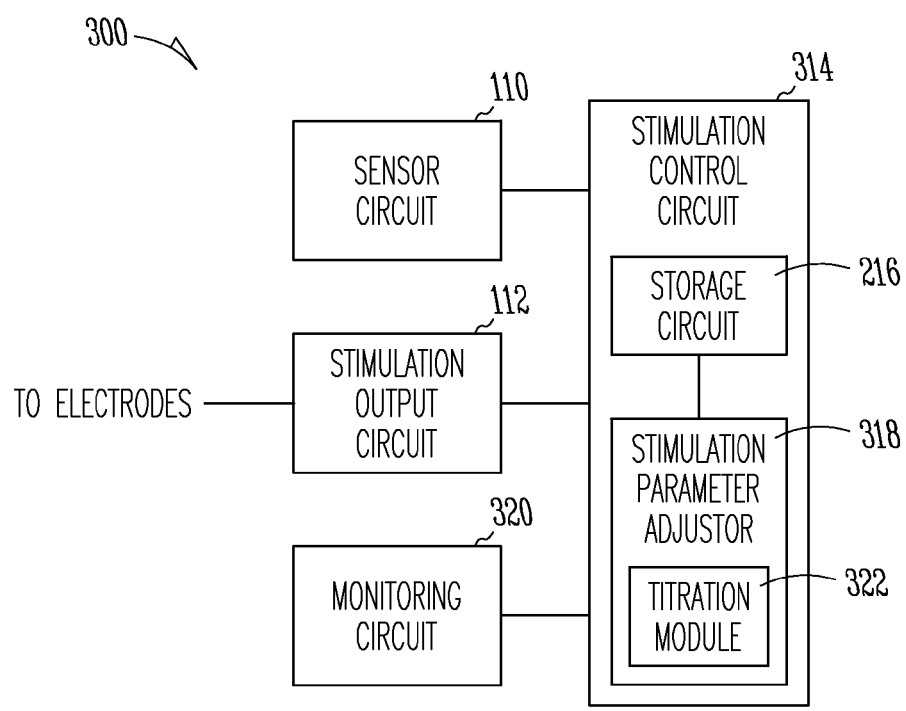
FIG. 3 is a block diagram illustrating another embodiment of the neurostimulation system.

FIG. 3 is a block diagram illustrating an embodiment of a neurostimulation system 300. System 300 represents an embodiment of system 200 and includes sensor circuit 110, stimulation output circuit 112, a monitoring circuit 320, and a stimulation control circuit 314. In addition to applying the neurostimulation according to the patient's physical state by system 200, system 300 provides for titration of the neurostimulation according to the patient's physical state.

Monitoring circuit 320 monitors one or more physiological signals each as a function of the sensor parameter. The one or more physiological signals are each indicative of one or more effects of the neurostimulation. In various embodiments, the one or more effects of the neurostimulation include one or more intended effects (therapeutic targets of the neuro stimulation) and/or one or more side effects (unintended effects). Monitoring circuit 320 senses the one or more physiological signals and produces one or more intended effect parameters and/or one or more side effect parameters using the sensed one or more physiological signals. The one or more intended effect parameters are each representative of a degree of one of the one or more intended effects. The one or more side effect parameters are each representative of a degree of one of the one or more the side effects. Monitoring circuit 320 is further discussed below, with reference to FIG. 7.

Stimulation control circuit 314 represents an embodiment of stimulation circuit 214 and includes storage circuit 216 and a stimulation parameter adjustor 318. Stimulation parameter adjustor 318 includes a titration module 322 that performs the titration of the neurostimulation. Titration module 322 performs the titration of the neurostimulation using the one or more physiological signals sensed by monitoring circuit 320. In various embodiments, titration module 322 performs the titration of the neurostimulation by approximately optimizing a value for each of the one or more sensor-driven parameters for a predefined value of the sensor parameter using one or more parameters selected from the one or more side effect parameters and the one or more intended effect parameters produced by monitoring circuit 320. In one embodiment, titration module 322 approximately optimizes the value for each of the one or more sensor-driven parameters for the predefined value of the sensor parameter using at least one of the one or more side effect parameters. In another embodiment, titration module 322 approximately optimizes the value for each of the one or more sensor-driven parameters for the predefined value of the sensor parameter using at least one of the one or more intended effect parameters. In another embodiment, titration module 322 approximately optimizes the value for each of the one or more sensor-driven parameters for the predefined value of the sensor parameter using at least one of the one or more intended effect parameters and at least one of the one or more side effect parameters. In another embodiment, titration module 322 approximately optimizes the value for each of the one or more sensor-driven parameters for the predefined value of the sensor parameter using one or more trends of the one or more side effect parameters and/or the one or more effectiveness parameters.

In one embodiment, titration module 322 performs the titration of the neurostimulation by approximately optimizing a value for each of the one or more sensor-driven parameters for each predefined value of the plurality of predefined values of the sensor parameter to provide a complete set of sensor-dependent values for the one or more sensor-driven parameters and the plurality of predefined values of the sensor parameter. In various embodiments, titration module 322 performs the titration of the neurostimulation for each of the one or more sensor-driven parameters in response to user commands, according to a specified schedule, and/or in response to detected opportunities.

Figure 4:
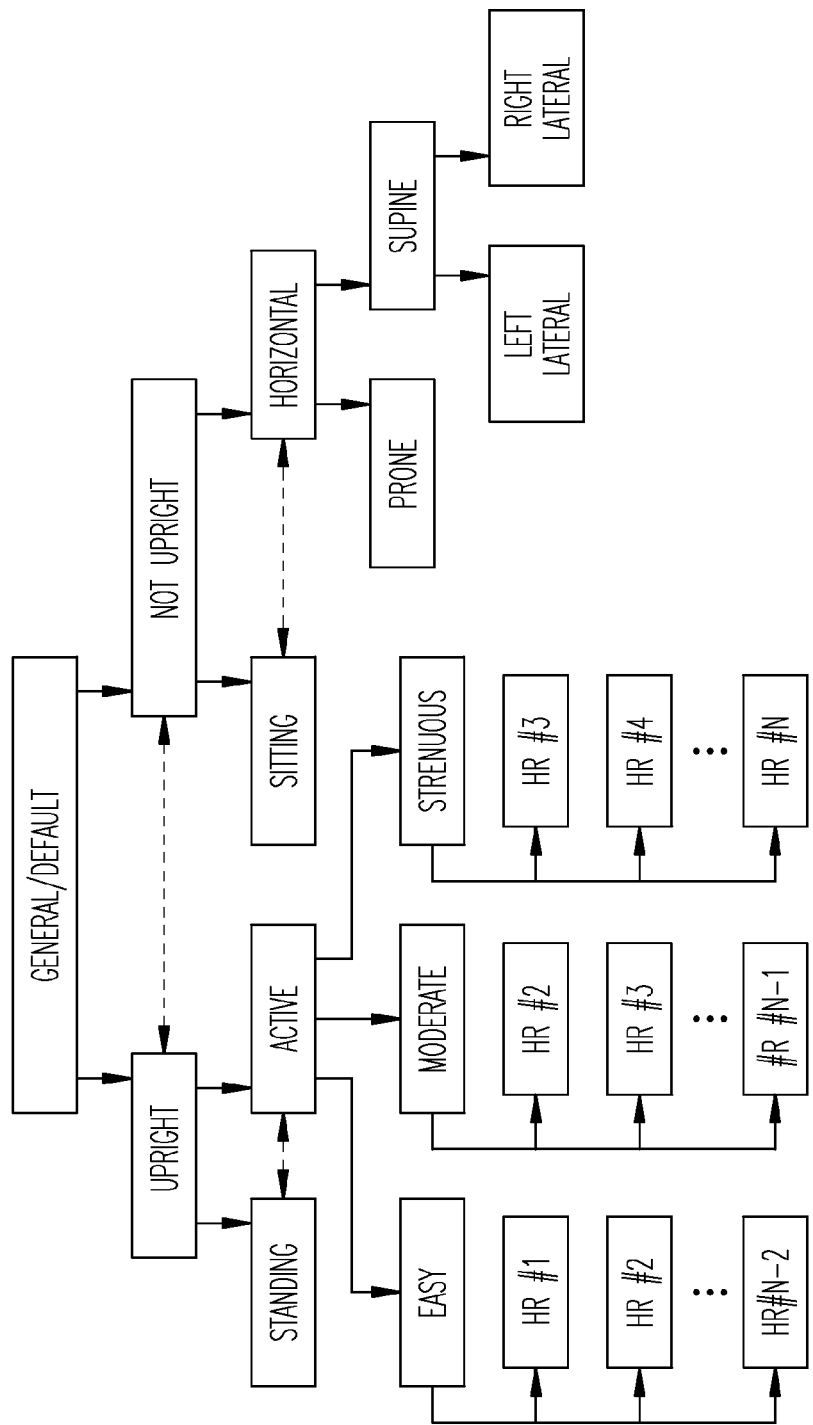
FIG. 4 is an illustration of an embodiment of a tree of predefined values of a sensor parameter.

FIG. 4 is an illustration of an embodiment of a tree of the plurality of predefined values of the sensor parameter. Each value of the plurality of predefined values of the sensor parameter represents a specific physical state of the patient, such as a specific posture, a specific range of activity level, or a combination of a specific posture and a specific range of activity level. Sensor circuit 110 produces the sensor parameter by selecting one of the predefined values using the sensed signal, which represents one or more signals indicative of the patient's physical state.

As illustrated in FIG. 4, the predefined values are assigned to predefined levels on the tree. The levels generally correspond to degrees of specificity in describing the physical state. In the illustrated embodiment, for example, the top level includes a "general/default" (e.g., undetermined) physical state, the next level includes postures of "upright" and "not upright", the next level under "upright" includes posture/activity of "standing" and "active", and so forth. In various embodiments, examples of the predefined values of the sensor parameter include upright, upright with activity, prone, supine, left lateral supine, right lateral spine, sitting, walking, and running. In various embodiments, examples of the predefined values of the sensor parameter further include transitional values for a transitional period during which the patient's physical state changes. In various embodiments, the patient's activity level is measured by, for example, acceleration, transthoracic impedance, minute ventilation, heart rate, or various combinations thereof.

Figure 5:
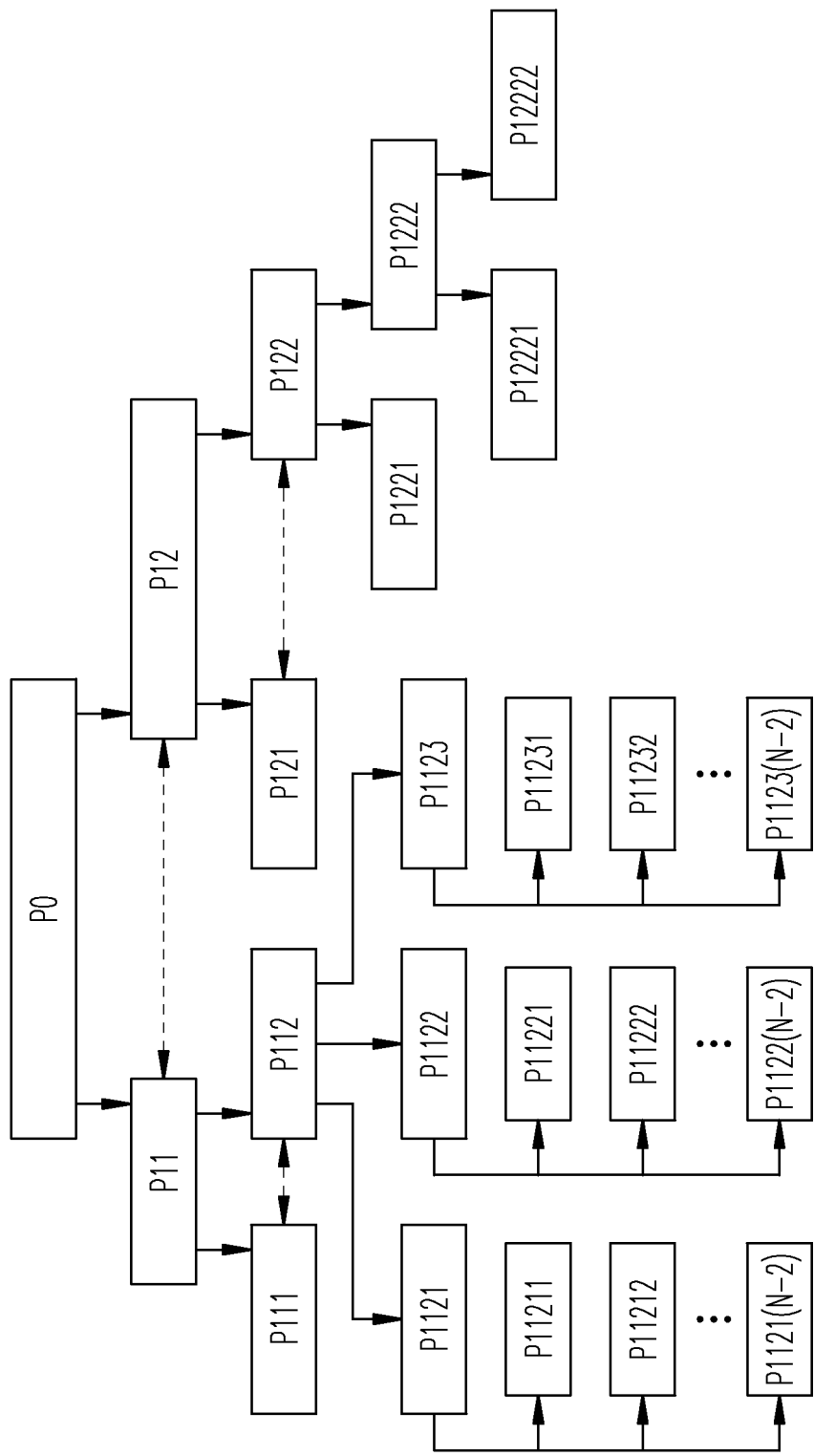
FIG. 5 is an illustration of an embodiment of a decision tree for selecting values of a stimulation parameter.

FIG. 5 is an illustration of an embodiment of a decision tree for selecting sensor-dependent values of a sensor-driven parameter of the stimulation parameters. In the illustrated embodiment, the sensor-dependent values each correspond to one of the predefined values of the sensor parameter. The sensor-dependent values each belong to a predefined level on the decision tree corresponding to the predefined levels on the tree of sensor parameter illustrated in FIG. 4. For example, corresponding to the tree illustrated in FIG. 4, examples of the sensor-dependent values for the sensor-driven parameter include at the top level a value "P0" for the general/default physical state at the top level, at the next level value "P11" for "upright" and a value "P12" for "not upright", at the next level under "upright" a value "P111" for "standing" and a value "P112" for "active", and so forth. In various embodiments in which the predefined values of the sensor parameter further include transitional values, the sensor-driven parameter also has transitional values each corresponding to one of the transitional values of the sensor parameter.

In one embodiment, the sensor-dependent values are each the value of the sensor-driven parameter corresponding to one of the predefined values of the sensor parameter. In another embodiment, the sensor-dependent values are each an offset to be added to a base value of the sensor-driven parameter corresponding to one of the predefined values of the sensor parameter.

In various embodiments, stimulation parameter adjustor 318 receives the current value of the sensor parameter from sensor circuit 110 and adjusts the sensor-dependent values of each of the one or more sensor-driven parameters according to the current value of the sensor parameter using the trees illustrated in FIGS. 4 and 5. The current value is assigned to one of the predefined values on the tree illustrated in FIG. 4 by sensor circuit 110. In one embodiment, the trees are stored in storage circuit 216, and stimulation parameter adjustor 318 selects one or more values from the stored sensor-dependent values for the one or more sensor parameters using the current value of the sensor parameter. In one embodiment, stimulation parameter adjustor 318 detects a change in the value of the sensor parameter and adjusts the one or more sensor-driven parameters in response to each detection of the change in the current value of the sensor parameter. In one embodiment, stimulation parameter adjustor 318 declares a detection of the change in the current value of the sensor parameter in response to a detection that the value of the sensor parameter has changed to a new value for at least a specified duration.

In various embodiments, stimulation parameter adjustor 318 uses the trees (as illustrated in FIGS. 4 and 5) stored in storage circuit 216 to map the current value of the sensor parameter to a sensor-dependent value for each of the one or more sensor-driven parameters. After the stored sensor-dependent value is identified by the mapping, stimulation parameter adjustor 318 determines whether the identified stored sensor-dependent value is currently optimal. In one embodiment, the stored sensor-dependent value is considered to be currently optimal if that value has been approximately optimized during a titration of the neurostimulation performed by titration module 322 for the current value of the sensor parameter. In another embodiment, the stored sensor-dependent value is considered to be currently optimal if that value has been approximately optimized during a titration of the neurostimulation performed by titration module 322 for the current value of the sensor parameter within a specified period of time. Stimulation parameter adjustor 318 selects the identified stored sensor-dependent value to control the delivery of the neurostimulation in response to that value being determined to be currently optimal. In response to the identified stored sensor-dependent value being determined not to be currently optimal, stimulation parameter adjustor 318 selects the sensor-dependent value corresponding to a higher level of the predefined value of the sensor parameter on the tree illustrated in FIG. 4. For example, if the current value of the sensor parameter is "standing", but the stored sensor-dependent value P111 is determined not to be currently optimal, stimulation parameter adjustor 318 selects the stored sensor-dependent value P11 if P11 is determined to be currently optimal. If P11 is determined not to be currently optimal, stimulation parameter adjustor 318 selects the value P0, which is the general or default value assigned to the sensor-driven parameter. In one embodiment, P0 is generally titrated for the neurostimulation such that it can be safely applied when the value of the sensor parameter is unavailable or considered unreliable. In one embodiment, in response to the identified stored sensor-dependent value being determined not to be currently optimal, stimulation parameter adjustor 318 initiates a titration of the neurostimulation for the current value of the sensor parameter. The titration is performed by titration module 322 while the value of the sensor parameter remains at the current value. In response to detection of a change in the current value of the sensor parameter, stimulation parameter adjustor 318 aborts the titration of the neurostimulation without updating the sensor-dependent value of each of the one or more sensor-driven parameters corresponding to the current value of the sensor parameter.

Figure 6:
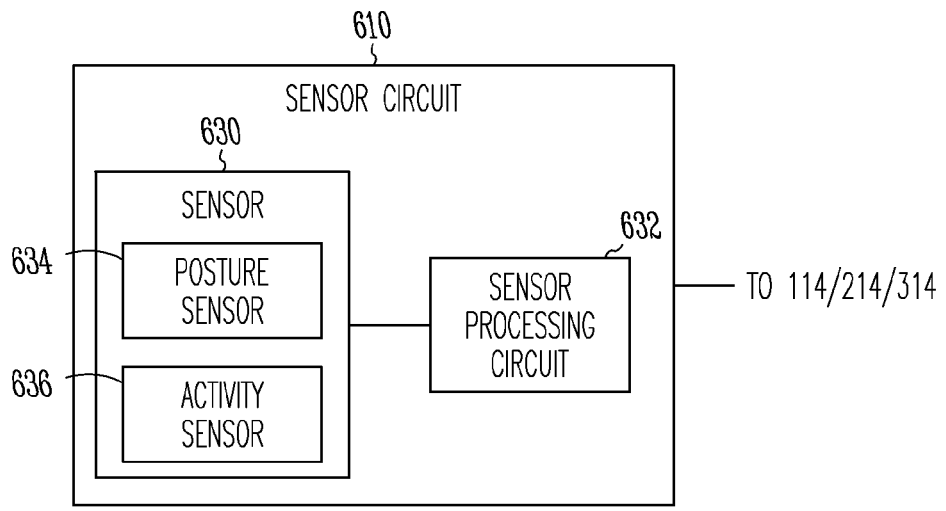
FIG. 6 is a block diagram illustrating an embodiment of a sensor circuit of the neurostimulation system.

FIG. 6 is a block diagram illustrating an embodiment of a sensor circuit 610. Sensor circuit 610 represents an embodiment of sensor circuit 110 and includes a sensor 630 and a sensor processing circuit 632. Sensor 630 includes one or more sensors to sense the signal indicative of the physical state of the patient. Sensor processing circuit 632 sets the current value of the sensor parameter representing the physical state to one of the predefined values of the sensor parameter using the sensed signal. Sensor 630 represents one or more sensors, and the signal indicative of the physical state of the patient represents one or more signals each sensed by one of the one or more sensors. In the illustrated embodiment, sensor 630 includes a posture sensor 634 to sense a posture signal indicative of a posture of the patient and an activity sensor 636 to sense an activity signal indicative of an activity level of the patient. In various embodiments, sensor 630 includes any one or more sensors capable of sensing one or more signals each indicative of a measure of the patient's physical state that affects result of the neurostimulation. Examples of such one or more sensors include one or more of an accelerometer, a respiratory sensor (minute ventilation sensor), a posture sensor, a heart rate sensor, a thoracic impedance sensor, and a metabolic demand sensor. Examples of posture sensor are discussed in U.S. Pat. No. 7,471,290, entitled "POSTURE DETECTION SYSTEM" and U.S. Patent Application Publication No. 2007/0118056 A1, entitled "POSTURE DETECTOR CALIBRATION AND USE", both assigned to Cardiac Pacemakers, Inc., which are incorporated herein by reference in their entirety. In various embodiments, each predefined value of the sensor parameter is a function of the signals sensed by the any one or more sensors.

Figure 7:
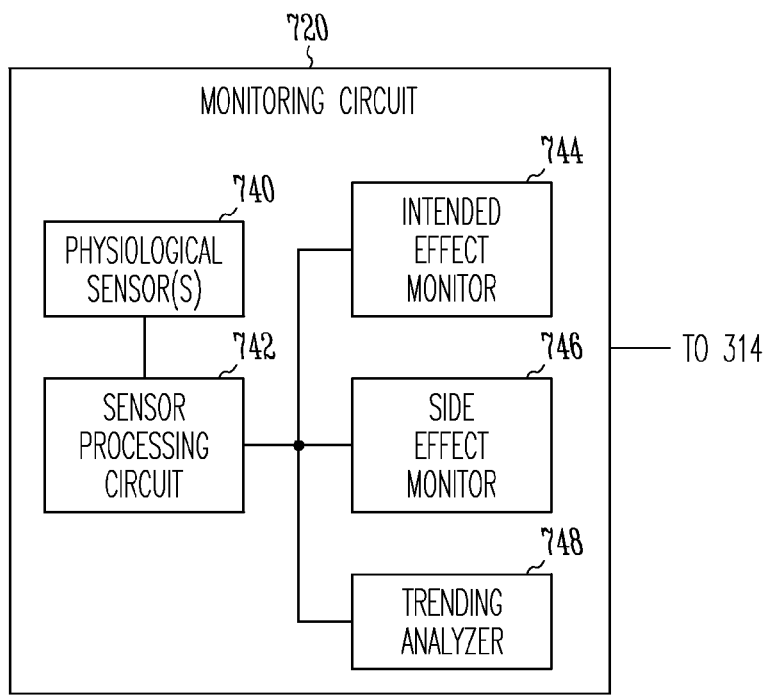
FIG. 7 is a block diagram illustrating an embodiment of a monitoring circuit of the neurostimulation system.

FIG. 7 is a block diagram illustrating an embodiment of a monitoring circuit 720. Monitoring circuit 720 represents an embodiment of monitoring circuit 320 and includes one or more physiological sensors 740, a sensor processing circuit 742, an intended effect monitor 744, a side effect monitor 746, and a trending analyzer 748. Physiological sensor(s) 740 senses one or more physiological signals each indicative of one or more effects of the neurostimulation. In various embodiments, the one or more effects of the neurostimulation include one or more of intended effects and/or side effects. Sensor processing circuit 742 processes the one or more physiological signals. In various embodiments, the one or more signals are each a function of the patient's physical state.

Intended effect monitor 744 produces one or more intended effect parameters using the one or more physiological signals. The one or more intended effect parameters are each representative of the degree of an intended effect caused by the neurostimulation. In one embodiment, the one or more intended effect parameters are indicative of whether the intended effect is within a target range specified by one or more thresholds. Intended effect monitor 744 determines whether the intended effect is within the target range using the one or more intended effect parameters and the one or more thresholds.

Side effect monitor 746 produces one or more side effect parameters using the one or more physiological signals. The one or more side effect parameters are each representative of the degree of a side effect caused by the neurostimulation. In one embodiment, the one or more side effect parameters are indicative of whether the side effect is within a tolerable range specified by one or more thresholds. Side effect monitor 746 determines whether the side effect is within the tolerable range using the one or more side effect parameters and the one or more thresholds.

Trending analyzer 748 produces one or more trends for one or more parameters each as a function of the sensor parameter. The trended one or more parameters are selected from the one or more intended effect parameters and the one or more side effect parameters.

Figure 8:
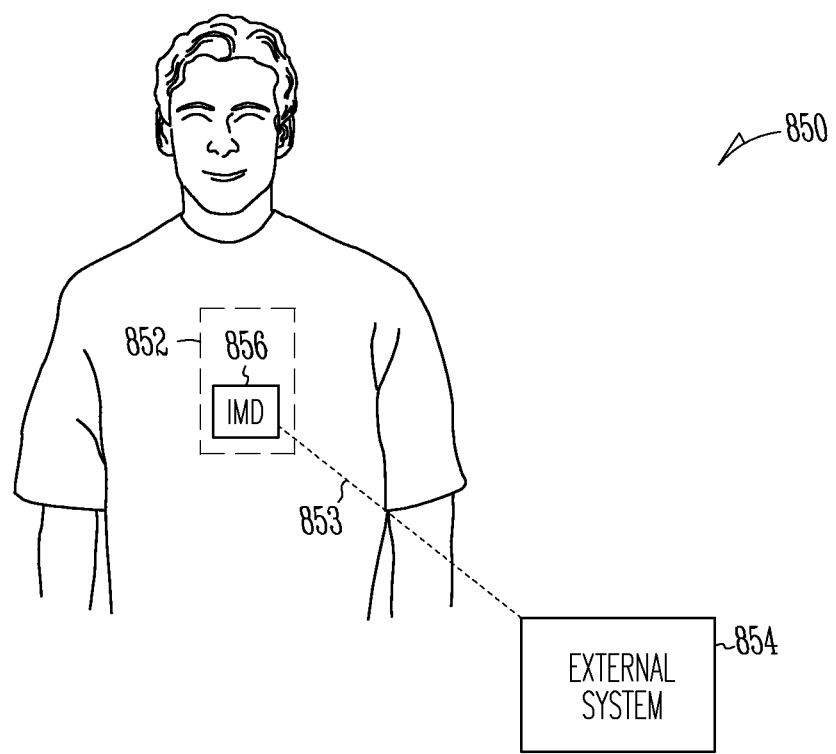
FIG. 8 is an illustration of an embodiment of an implantable system including the neurostimulation system and portions of an environment in which the implantable system is used.

FIG. 8 is an illustration of an embodiment of an implantable device system 850 and portions of an environment in which system 850 is used. System 850 includes system 100 including its various embodiments as discussed in this document.

System 850 includes an implantable system 852 and an external system 854. Implantable system 852 includes an implantable medical device (IMD) 856. External system 854 and IMD 856 communicate via a telemetry link 853. In various embodiments, implantable system 856 includes system 100, 200, or 300. In various embodiments, IMD 856 integrates a cardiac rhythm management (CRM) device with a neural sensing and stimulation device including portions of system 100, 200, or 300. The CRM device senses cardiac electrical activities and delivers cardiac stimulation. Examples of the CRM device include pacemakers, cardioverter/defibrillators, combined pacemaker-cardioverter/defibrillators, cardiac resynchronization therapy (CRT) devices, and cardiac remodeling control therapy (RCT) devices. In various embodiments, neural activities are sensed to indicate a need for cardiac stimulation and/or to control the timing of pacing pulse deliveries. In various embodiments, cardiac activities are sensed to control the timing of neural stimulation pulse deliveries, such as to synchronize neural stimulation to cardiac cycles.

Figure 9:
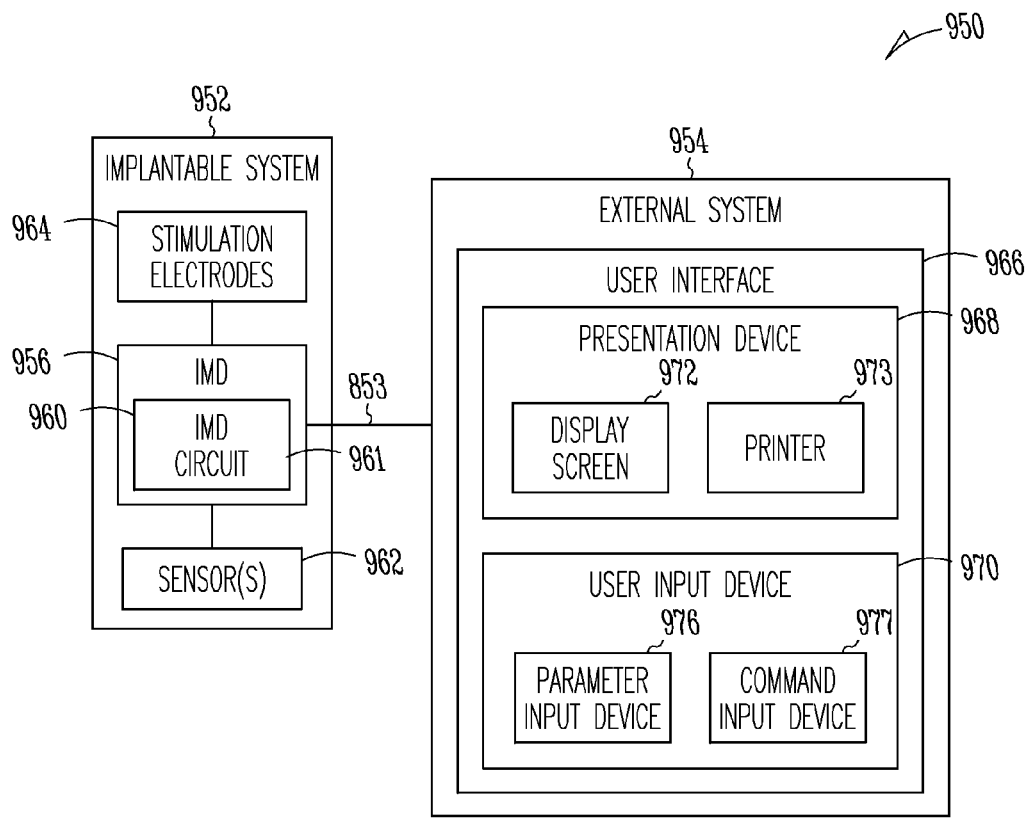
FIG. 9 is a block diagram illustrating an embodiment of the implantable system.

FIG. 9 is a block diagram illustrating an embodiment of an implantable device system 950. System 950 represents an embodiment of system 850 and includes an implantable system 952 and an external system 954.

Implantable system 952 represents an embodiment of implantable system 852 and includes stimulation electrodes 964, an IMD 956, and one or more sensors 962. Stimulation electrodes 964 allow for delivery of the neurostimulation from IMD 956. IMD 956 represents an embodiment of IMD 856 and includes an IMD circuit 960 and an implantable housing 961 encapsulating IMD circuit 960. In one embodiment, IMD circuit 960 includes at least stimulation output circuit 112 and stimulation control circuit 114, 214, or 314. In another embodiment, IMD circuit 960 further includes monitoring circuit 320 or 720. Sensor(s) 962 represents sensor 630 and physiological sensor(s) 740. In various embodiments, sensor(s) 962 includes one or more sensors external to implantable housing 961, one or more sensors encapsulated within implantable housing 961, or sensors both external to and encapsulated within implantable housing 961. In various embodiments, IMD circuit 960 includes various elements of system 100, 200, or 300.

External system 954 is an embodiment of external system 854 and is communicatively coupled to IMD 956 via telemetry link 853. External system 954 includes a user interface 966. User interface 966 includes a presentation device 968 and a user input device 970. Presentation device 968 presents, for example, the signal indicative of the patient's physical state, the sensor parameter, the monitored one or more physiological signals, the intended effect parameter, the side effect parameter, and/or trends of such signals and parameters. In the illustrated embodiment, presentation device 968 includes a display screen 972 and a printer 973. User input device 970 includes a parameter input device 976 and a command input device 977. Parameter input device 976 allows a user to enter the sensor-dependent values for each of the one or more sensor-driven parameters for the predefined values of the sensor parameter. Command input device 977 allows the user to enter commands controlling the operation of system 950, such as a command for initiating the titration of the neuro stimulation.

In one embodiment, external system 954 includes a programmer including user interface 966. In one embodiment, external system 954 includes a patient management system including an external device communicatively coupled to IMD 956 via telemetry link 853 and a remote device in a distant location and communicatively coupled to the external device via a communication network. The external device and/or the remote device include user interface 966.

FIGS. 10-32 illustrate various embodiments of methods for titration and applying neurostimulation that are performed by operating the systems and system components discussed above with reference to FIGS. 1-9. In various embodiments, system 100, including its various embodiments as discussed above, is configured to perform one or more methods discussed below with reference to FIGS. 10-32. Such system configuration includes, for example, programming sensor circuit 110 or 610, stimulation controller 114, 214, or 314, and/or monitoring circuit 320 or 720, to perform the one or more methods.

Figure 10:
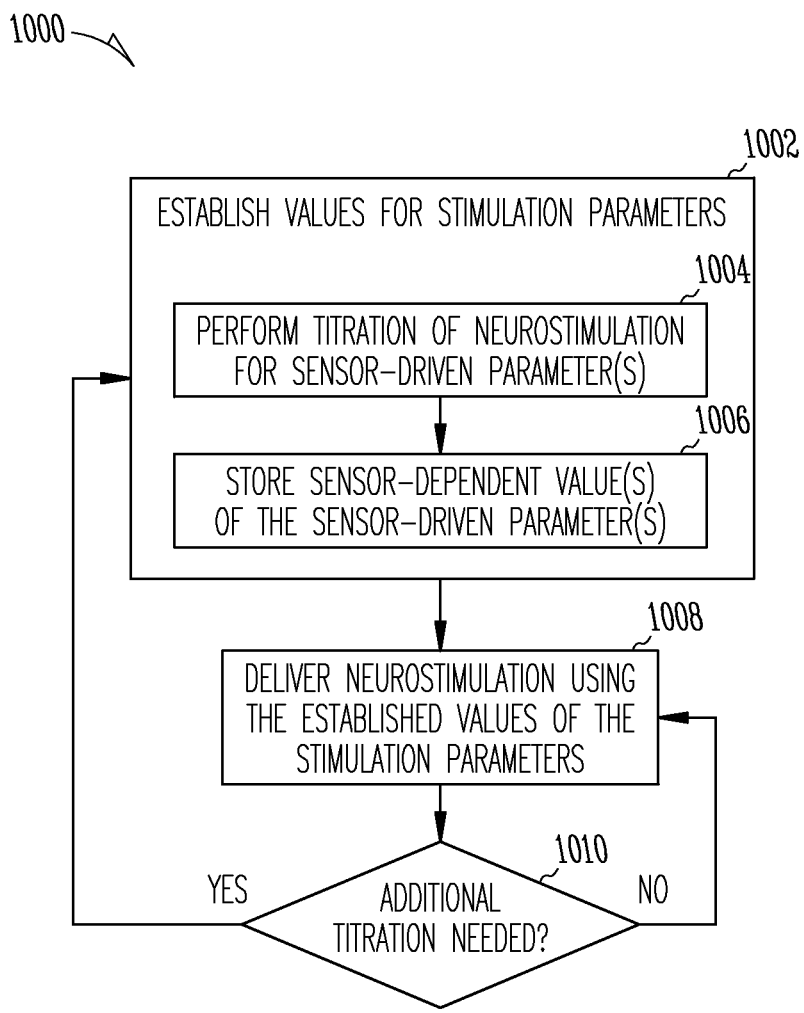
FIG. 10 is a flowchart illustrating an embodiment of a method for neurostimulation.

FIG. 10 is a flowchart illustrating an embodiment of a method 1000 for neurostimulation. Method 100 provides for titration and application of neurostimulation according to the patient's physical state.

At 1002, values for a plurality of stimulation parameters are established. The stimulation parameters are used to control delivery of the neurostimulation and include one or more sensor-driven parameters each having sensor-dependent values corresponding to values of a sensor parameter representative of the patient's physical state. The establishment of the values of the one or more sensor-driven parameters includes performing titration of the neurostimulation at 1004 for each of the values of the sensor parameter. If the titration results in one or more new sensor-dependent values, at 1006 the one or more new sensor-dependent values are stored. At 1008, the neurostimulation is delivered using the established values of the stimulation parameters including the one or more sensor-driven parameters. A stored sensor-dependent value for the one or more sensor-driven parameters is selected for a current value of the sensor parameter. At 1010, whether additional titration of the neurostimulation is needed is determined based on whether the stored sensor-dependent values for the one or more sensor-driven parameters have been approximately optimized for the current values of the sensor parameter by the titration of the neurostimulation. Step 1002 is repeated until no additional titration is needed. For example, if the stored sensor-dependent value for the one or more sensor-driven parameters selected for the current value of the sensor parameter is determined not to be currently optimal, step 1002 is repeated at least to update that stored sensor-dependent value.

Figure 11:
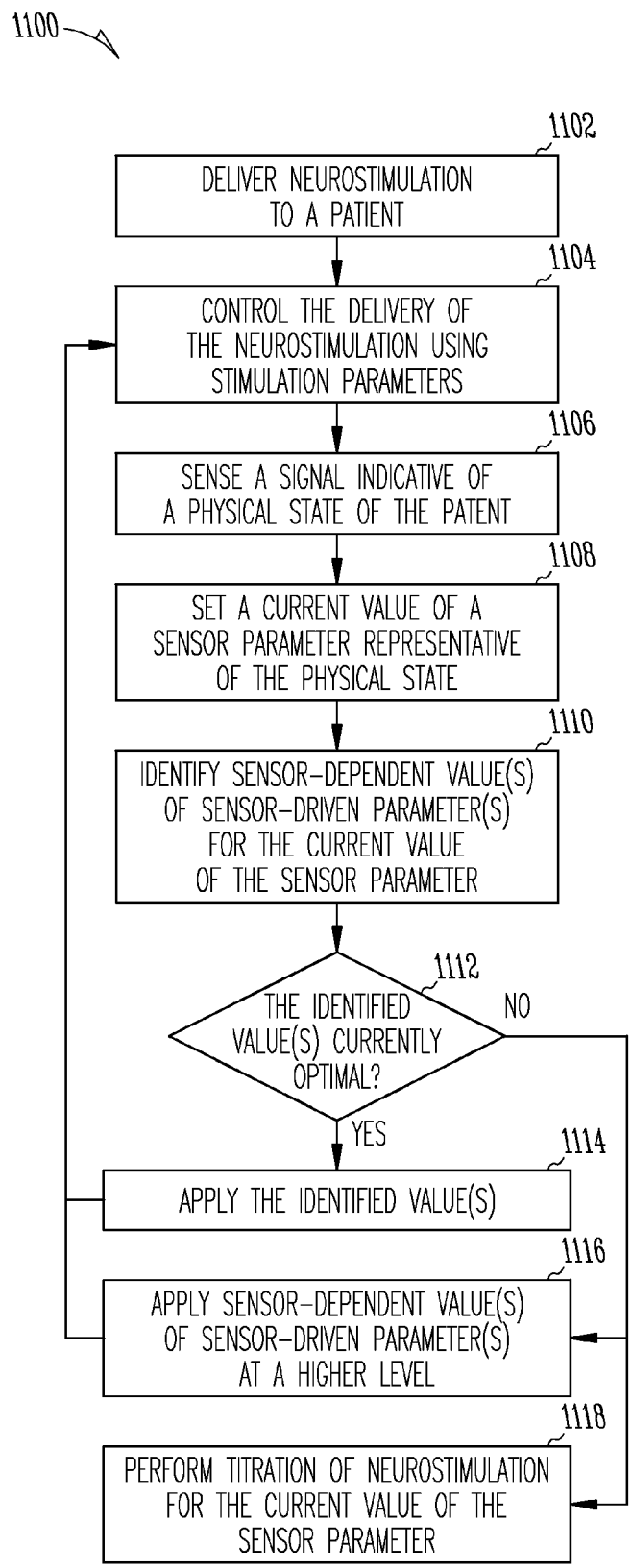
FIG. 11 is a flowchart illustrating another embodiment of the method for neurostimulation.

FIG. 11 is a flowchart illustrating an embodiment of a method 1100 for neurostimulation. Method 1100 represents an embodiment of method 1000 and provides for titration and application of the neurostimulation according to the patient's physical state.

At 1102, the neurostimulation is delivered to the patient. At 1004, the delivery of the neurostimulation is controlled using the plurality of stimulation parameters. The plurality of stimulation parameters includes the one or more sensor-driven parameters having sensor-dependent values each corresponding to a predefined value of the sensor parameter representing the patient's physical state. In one embodiment, the sensor-dependent values are values of the one or more sensor-driven parameters. In another embodiment, the sensor-dependent values are offsets each to be added to a base value of a parameter of the one or more sensor-driven parameters corresponding to one of the predefined values of the sensor parameter.

At 1006, a signal indicative of the physical state of the patient is sensed. In various embodiments, this signal represents one or more of a posture signal indicative of a posture of the patient and an activity signal indicative of an activity level of the patient. In various embodiments, this signal is sensed using, for example, one or more of an accelerometer, a respiratory sensor (minute ventilation sensor), a posture sensor, a heart rate sensor, a thoracic impedance sensor, and a metabolic demand sensor. At 1008, the sensor parameter is set to its current value determined using the sensed signal. In one embodiment, this includes identifying a predefined value of the sensor parameter from the tree of the predefined values of the sensor parameter illustrated in FIG. 4, on which the predefined values each belong to a level associated with specificity in describing the physical state.

At 1110, one or more sensor-dependent values of the one or more sensor-driven parameters are identified from stored parameter values. In one embodiment, this is done by mapping the current value of the sensor parameter to the corresponding one or more sensor-dependent values of the one or more sensor-driven parameters using the trees illustrated in FIGS. 4 and 5. In one embodiment, the one or more sensor-driven parameters have transitional values each specified for use while the sensor parameter is changing from the current value to a new value.

At 1112, whether the identified one or more sensor-dependent values are currently optimal is determined. In one embodiment, a sensor-dependent value is currently optimal if it has been approximately optimized by the titration of the neurostimulation. In another embodiment, a sensor-dependent value is currently optimal if it has been approximately optimized by the titration of the neurostimulation performed within a specified time period.

At 1114, if determined to be currently optimal, the identified one or more sensor-dependent values are applied to control the delivery of the neurostimulation. At 1116, if determined not to be currently optimal, one or more sensor-dependent values at a higher level of the decision tree as illustrated in FIG. 5 are applied to control the delivery of the neurostimulation. At 1118, if determined not to be currently optimal, the titration of the neurostimulation is performed to approximately optimize the identified one or more sensor-dependent values. Various embodiments of the method for performing the titration of the neurostimulation are discussed below, with reference to FIGS. 12-15. The titration of the neurostimulation provides for approximate optimization of the sensor-driven parameters for the predefined values of the sensor parameter.

Figure 12:
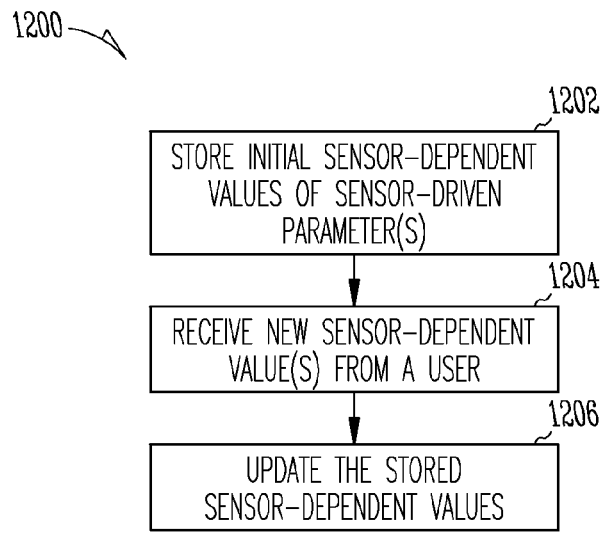
FIG. 12 is a flowchart illustrating an embodiment of a method for titration of neurostimulation.

FIG. 12 is a flowchart illustrating an embodiment of a method 1200 for the titration of the neurostimulation. At 1202, initial sensor-dependent values for the sensor-driven parameters are stored. In one embodiment, the initial sensor-dependent values are default values that are generally titrated for the predefined values of the sensor parameter. At 1204, one or more new sensor-dependent values are received from the user. In various embodiments, the user decides one or more approximately optimal values for the sensor-driven parameters using available manual or automatic means of titration. At 1206, the stored sensor-dependent values are updated with the one or more approximately optimal values. Steps 1204 and 1206 are repeatable to allow for updating the stored sensor-dependent values when one or more new sensor-dependent values become available to the user.

Figure 13:
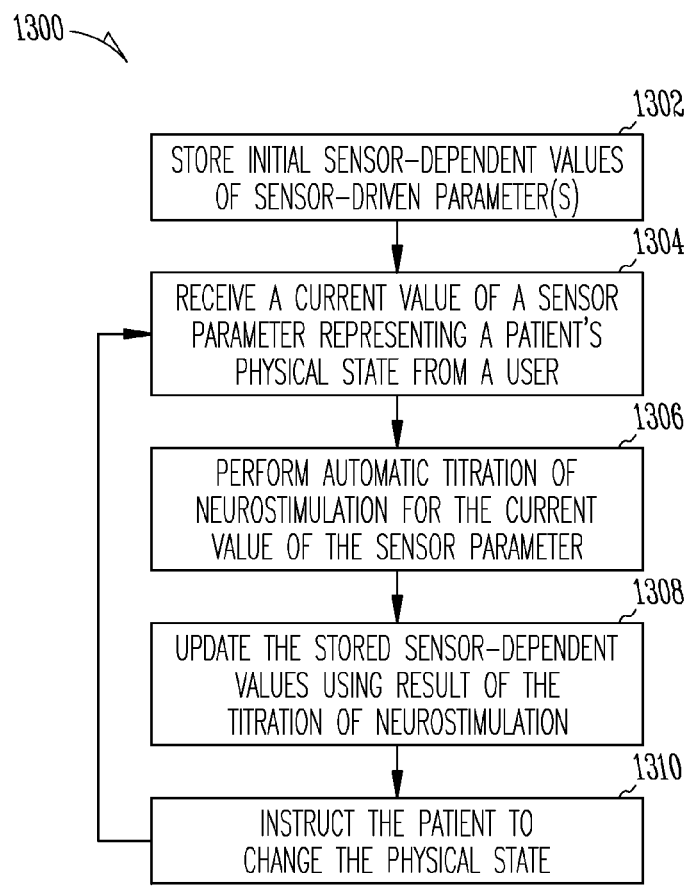
FIG. 13 is a flowchart illustrating another embodiment of the method for titration of neurostimulation.

FIG. 13 is a flowchart illustrating an embodiment of a method 1300 for the titration of the neurostimulation. At 1302, initial sensor-dependent values for the sensor parameters are stored. In one embodiment, the initial sensor-dependent values are default values that are generally titrated for the predefined values of the sensor parameter. At 1304, the current value of the sensor parameter is received from the user, who observes the patient's physical state. In one embodiment, this includes receiving a confirmation from the user on the correctness of the current value that is automatically generated based on a sensed signal. At 1306, an automatic titration of the neurostimulation is performed for the current value of the sensor parameter received from the user. The automatic titration is discussed below, with reference to FIG. 15. At 1308, the stored sensor-dependent values are updated using the result of the automatic titration performed at 1306. At 1310, the patient is instructed by the user to change the physical state, for example from sitting to standing, and steps 1304-1308 are repeated for the new physical state. Steps 1304 to 1310 are repeatable to allow for updating the stored sensor-dependent values for all the predefined values of the sensor parameter.

Figure 14:
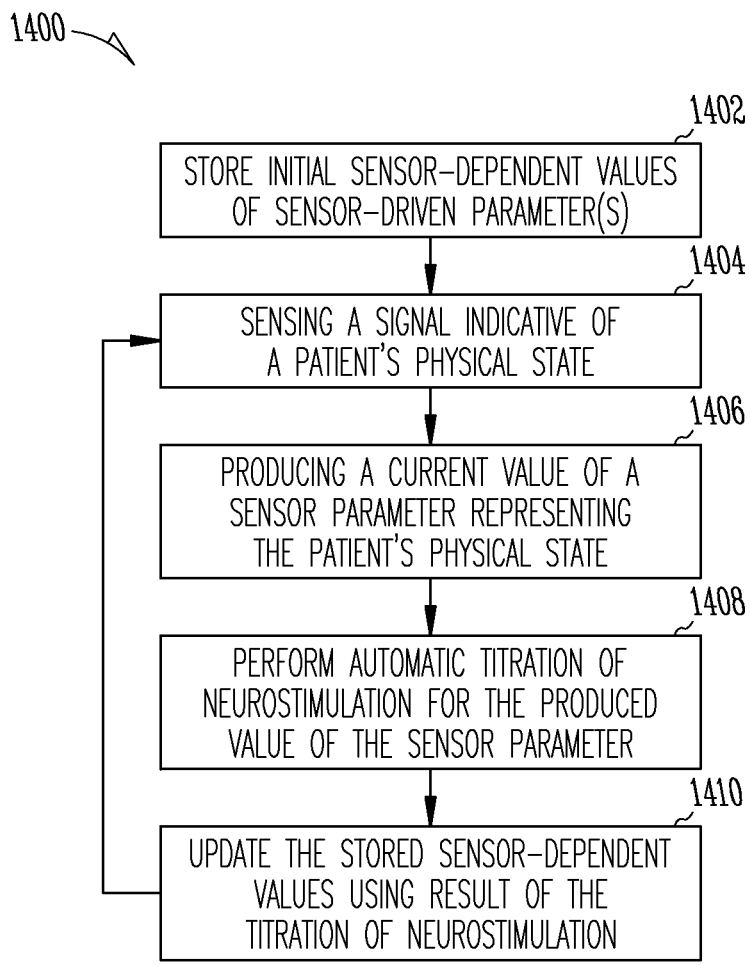
FIG. 14 is a flowchart illustrating another embodiment of the method for titration of neurostimulation.

FIG. 14 is a flowchart illustrating an embodiment of a method 1400 for the titration of the neurostimulation. At 1402, initial sensor-dependent values for the sensor parameters are stored. In one embodiment, the initial sensor-dependent values are default values that are generally titrated for the predefined values of the sensor parameter. At 1404, the signal indicative of the patient's physical state is sensed. At 1406, the current value of the sensor parameter is produced using the signal sensed at 1404. This includes selecting a value from a plurality of predefined values of the sensor parameter. At 1408, an automatic titration of the neurostimulation is performed for the current value of the sensor parameter received from the user. The automatic titration is discussed below, with reference to FIG. 15. At 1410, the stored sensor-dependent values are updated using the results of the automatic titration performed at 1406. Steps 1404 to 1410 are repeatable to allow for updating the stored sensor-dependent values for all the predefined values of the sensor parameter.

In one embodiment, steps 1404 to 1410 are repeated for all the predefined values of the sensor parameter to provide a complete set of sensor-dependent values for the one or more sensor-driven parameters that are currently optimal. In one embodiment, the patient changes the physical state as directed by the user to result in the automatic titration performed for all the predefined values of the sensor parameter. In another embodiment, the automatic titration is performed when an opportunity is detected, for example, when the patient remains at a particular physical state, and the automatic titration has not been performed, or has not been performed for a specified period of time, for that physical state. In one embodiment, whether to perform the automatic titration is determined in response to detection of a change in the sensor parameter from its current value to a new value. Whether the one or more sensor-dependent values of the one or more sensor-driven parameters corresponding to the new value of the sensor parameter are currently optimal are determined. In one embodiment, a sensor-dependent value is currently optimal if it has been approximately optimized for the new value of the sensor parameter. In another embodiment, a sensor-dependent value is currently optimal if it has been approximately optimized for the new value of the sensor parameter within a specified period of time. In one embodiment, performance of the automatic titration is initiated in response to the new value of the sensor parameter sustaining for at least a specified time interval. In one embodiment, performance of the automatic titration is aborted in response to the value of the sensor parameter changing during the automatic titration.

In various embodiments, one or more of methods 1200, 1300, and 1400 are performed to provide for a complete set of currently optimal sensor-dependent values for the one or more sensor-driven parameters corresponding to all the predefined values of the sensor parameter.

Figure 15:
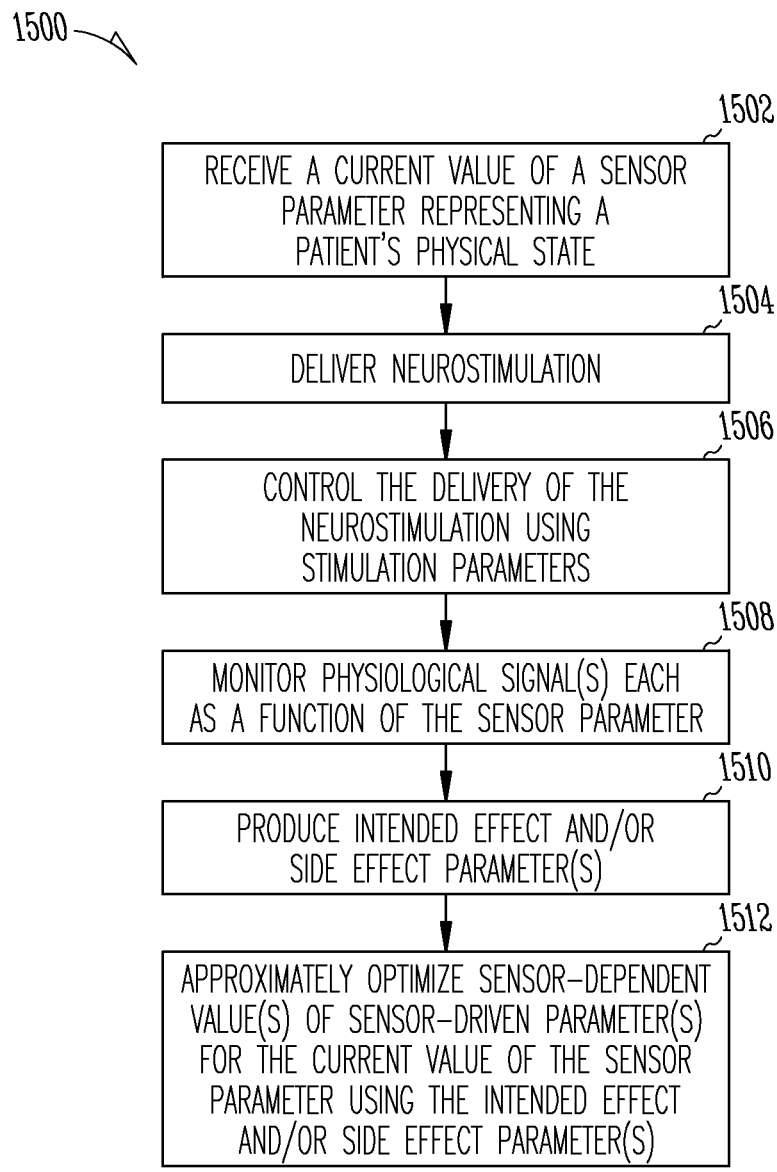
FIG. 15 is a flowchart illustrating an embodiment of a method for automatic titration of neurostimulation.

FIG. 15 is a flowchart illustrating an embodiment of a method 1500 for automatic titration of the neurostimulation. Method 1500 is performed to approximately optimize the one or more sensor-dependent values of the one or more sensor-drive parameters for the current value of the sensor parameter.

At 1502, the current value of the sensor parameter representing the patient's current physical state is received. At 1504, the neurostimulation is delivered. At 1506, the delivery of the neurostimulation is controlled using the plurality of stimulation parameters including the one or more sensor-drive parameters. In one embodiment, the delivery of the neurostimulation includes delivery of electrical stimulation pulses. Examples of the stimulation parameters include pulse amplitude, pulse width, pulse frequency or inter-pulse interval, duty cycle, and periodic dose. One or more of such parameters are sensor-driven.

At 1508, one or more physiological signals are monitored, each as a function of the sensor parameter. The one or more physiological signals are each indicative of an effect of the neurostimulation. At 1510, one or more intended effect parameters and/or one or more side effect parameters are produced using the sensed one or more physiological signals. The one or more intended effect parameters are each representative of a degree of the effectiveness of the neurostimulation. In one embodiment, the one or more intended effect parameters are each indicative of whether the therapeutic effect is within a target range specified by one or more thresholds. The one or more side effect parameters are each indicative of whether the side effect is within a tolerable range specified by one or more thresholds. In one embodiment, one or more parameters are trended each as a function of the sensor parameter. The one or more parameters are selected from the one or more intended effect parameters and the one or more side effectiveness parameters.

At 1512, the sensor-dependent value for each of the one or more sensor-driven parameters is approximately optimized for the current value of the sensor parameter. In one embodiment, the sensor-dependent value for each of the one or more sensor-driven parameters is approximately optimized for the current value of the sensor parameter using at least one of the one or more side effect parameters. For example, the sensor-dependent value is approximately optimized when the one or more side effect parameters are within the tolerable range. In another embodiment, the sensor-dependent value for each of the one or more sensor-driven parameters is approximately optimized for the current value of the sensor parameter using at least one of the one or more intended effect parameters. For example, the sensor-dependent value is approximately optimized when the one or more intended effect parameters are within the target range. In another embodiment, the sensor-dependent value for each of the one or more sensor-driven parameters is approximately optimized for the current value of the sensor parameter using at least one of the one or more side effect parameters and at least one of the one or more intended effect parameters. For example, the sensor-dependent value is approximately optimized when the one or more intended effect parameters are within the target range and the one or more side effect parameters are within the tolerable range.

Figure 16:
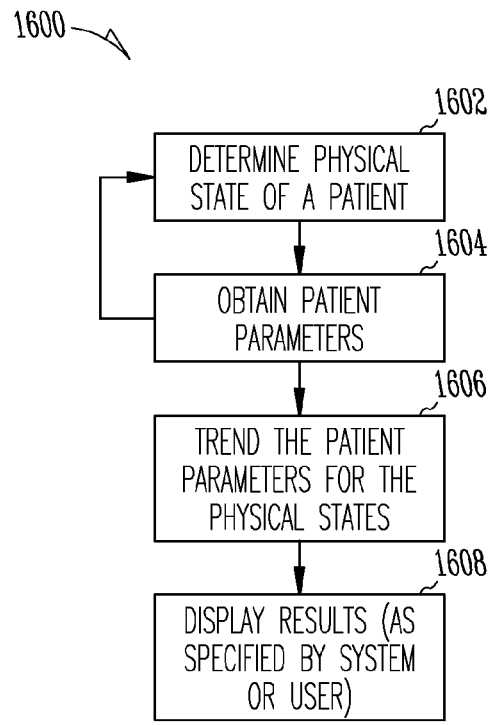
FIG. 16 is a flowchart illustrating an embodiment of a method for trending patient diagnostic information.

FIG. 16 is a flowchart illustrating an embodiment of a method 1600 for trending patient diagnostic information. The patient diagnostic information include various patient parameters including, but not limited to, the one or more intended effect parameters and the one or more side effect parameters.

At 1602, the patient's physical state is determined. In various embodiments, the physical state includes the patient's posture and/or activity level. At 1604, the patient parameters are obtained for the physical state. At 1606, the patient parameters are trended for the patient's various physical states. At 1608, the patient parameters and/or their trends are presented to the user in a way specified by the user. In various embodiments, the user applies such diagnostic information to titrate the neurostimulation for the patient.

In one embodiment, method 1600 is performed to assist the user in deciding whether the neurostimulation needs to be titrated according to the patient's physical state. Examples of the patient parameters obtained and trended include the patient's time spent in each physical state, duration of heart failure conditions, number of premature ventricular contractions, number and type of arrhythmia episodes, heart rate variability (e.g., measured by SDANN, LF/HF ratio), and blood pressure. The patient parameters are trended and/or displayed, on display screen 972 of use interface 966 for example, to show the effect of the patient's physical state on these parameters. In various embodiments, the user may vary the default display by system or disease type, select to group the physical states by types (e.g., erect, erect with activity, prone, supine, left lateral supine, right lateral supine, etc.), include trends for all physical states to compare with trends for a position and/or an activity level, and/or include indication when one trend varies significantly from other trends.

In one embodiment, method 1600 is performed to generate and trend patient parameters indicative of efficacy of the neurostimulation. Patient parameters indicative of the current condition of the patient are obtained, trended, and displayed. The user is allowed to adjust the display, for example, by changing time scale. The trends of the patient parameters may be annotated with one or more of the current level of the neurostimulation (represented by stimulation parameters such as amplitude or dosing), acceptable target range of the value for each of the patient parameters, times when the neurostimulation is adjusted (e.g., when IMD circuit 960 is reprogrammed), times when the dosing is approximately optimized for efficacy, and trend of the physical state. In various embodiments, the user may vary the default display by system or disease type, select to group the physical states by types (e.g., erect, erect with activity, prone, supine, left lateral supine, right lateral supine, etc.), include trends for all physical states to compare with trends for a position and/or an activity level, and/or include indication when one trend varies significantly from other trends. In one embodiment, diagnostic information is annotated with the current level of the neurostimulation (represented by stimulation parameters such as amplitude or dosing). Examples of such diagnostic information include time when the patient is at each physical state, system parameters, and patient parameters. Examples of the system parameters include system effectiveness of a combined pacing-neurostimulation device and pacing/sensing ratios. In various embodiments, the combined pacing-neurostimulation device provides atrial and ventricular pacing for cardiac rhythm management, including right atrial pacing, right ventricular pacing, left ventricular pacing, and biventricular pacing for cardiac resynchronization therapy. In various embodiments, the goal of the system is also annotated. It is noted that different systems may have different goals, such as 0% ventricular pacing desired versus 100% biventricular pacing desired. Examples of the patient parameters include heart rate, atrioventricular delay, interventricular delay, time in atrial fibrillation, numbers of premature ventricular contraction, supraventricular tachycardia, ventricular tachycardia, heart rate variability (e.g., Standard Deviation of Averages of Normal-to-Normal intervals (SDANN) and ratio of Low-Frequency HRV to High-Frequency HRV (LF/HF ratio)), respiratory sinus arrhythmia ratio, and blood pressure.

In one embodiment, system 100, including its various embodiments discussed in this document, is configured to perform method 1600. For example, sensor circuit 610 may be programmed to perform step 1602, monitoring circuit 720 may be programmed to perform steps 1604 and 1606, and user interface 966 may be programmed to perform step 1608.

Figure 17:
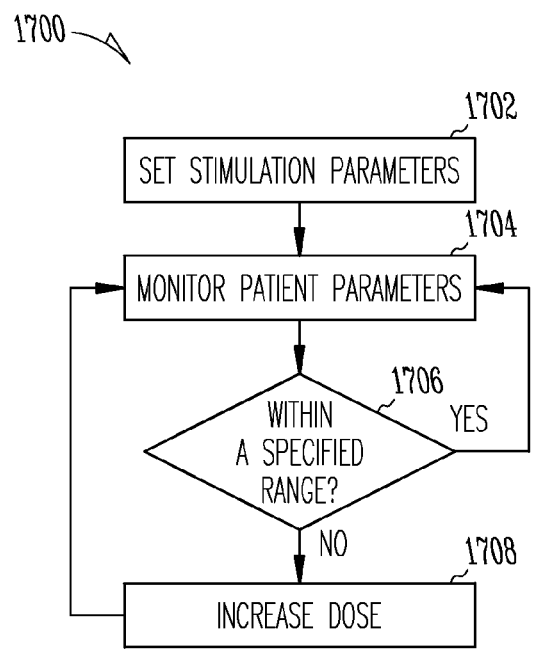
FIG. 17 is a flowchart illustrating an embodiment of a method for optimizing neurostimulation for chronic outcome.

FIG. 17 is a flowchart illustrating an embodiment of a method 1700 for optimizing neurostimulation for chronic outcome. The stimulation parameters used in method 1700 include the one or more sensor-driven parameters. Adjustment of the stimulation parameters includes adjustment of at least one of the one or more sensor-driven parameters.

At 1702, the stimulation parameters are set. In one embodiment, the initial values of the stimulation parameters are determined using acute titration methods such as by adjusting the stimulation parameters for desired level of laryngeal vibration and/or patient tolerance. At 1704, patient parameters indicative of the current condition of the patient are monitored. The patient parameters are monitored by a chronic measurement (rather than an acute response to a change in therapy). Examples of the patient parameters to be monitored include heart rate variability (e.g., SDANN and LF/HF ratio), blood pressure (e.g., pulmonary artery pressure), activity, temperature, respiratory sinus arrhythmia ratio, spectral turbulence, and thoracic impedance. In one embodiment, one or more parameters each being a blend of multiple patient parameters are monitored. In one embodiment, the patient parameters to be monitored include measure of device efficacy such as percentage of biventricular pacing (in a combined pacing-neurostimulation device). In one embodiment, a rolling average for each of selected one or more patient parameter is monitored. The duration of averaging may be short-term (e.g., 5 minutes, 10 minutes, 1 hour, 4 hours, or 1 day) or long-term (e.g., 1 week or 1 month).

At 1706, whether the values of the patient parameters are within a specified range (such as a target range) over a monitoring duration is determined. The monitoring duration may be mid-term to long-term, such as 1 week to 1 month. At 1708, the dose of the neurostimulation is increased in response to a determination at 1706 that the values of the patient parameters are not within the specified range. In one embodiment, the stimulation parameters are approximately optimized such that the values of the patient parameters are within the specified range. The sensor-driven parameters are approximately optimized by performing the titration of the neurostimulation as discussed above (e.g., methods discussed with reference to FIGS. 12-15). Whether the current condition of the patient improves after the dose increase is determined by repeating the monitoring at 1704. In one embodiment, steps 1704, 1706, and 1708 are repeated until the current condition of the patient improves such that the patient parameters become within the specified range.

In one embodiment, system 100, including its various embodiments discussed in this document, is configured to perform method 1700. For example, stimulation control circuit 314 may be programmed to perform steps 1702 and 1708, and monitoring circuit 720 may be programmed to perform steps 1704 and 1708.

Figure 18:
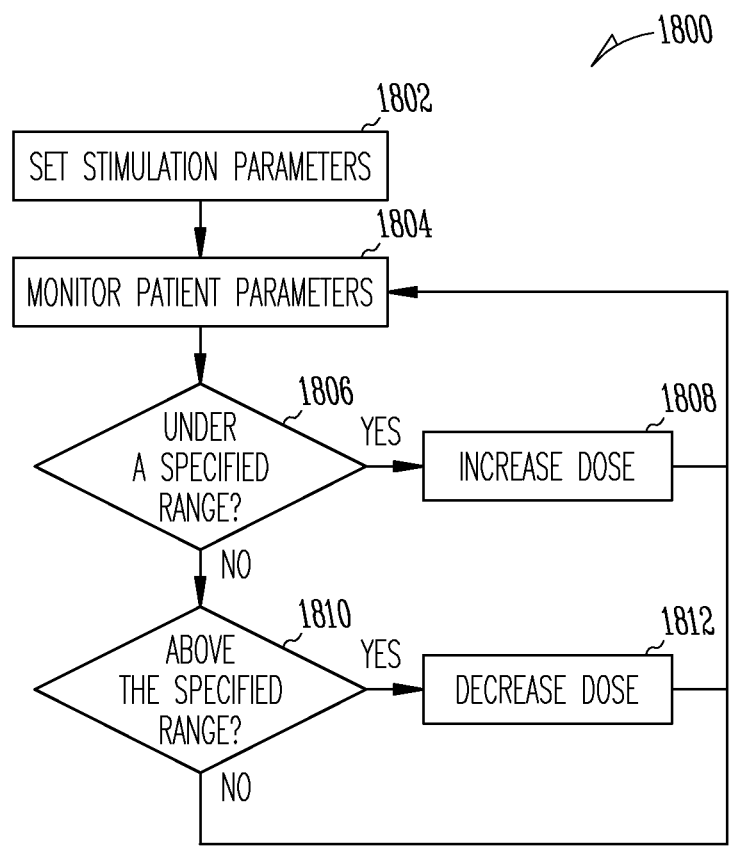
FIG. 18 is a flowchart illustrating another embodiment of the method for optimizing neurostimulation for chronic outcome.

FIG. 18 is a flowchart illustrating an embodiment of a method 1800 for optimizing neurostimulation for chronic outcome. Method 1800 is an embodiment of method 1700 and includes a further determination on whether the values of the patient parameters are each above or below its specified range.

At 1802, the stimulation parameters are set. At 1804, patient parameters indicative of the current condition of the patient are monitored. At 1806, whether the values of the patient parameters are below the specified range over the monitoring duration is determined. At 1808, the dose of the neurostimulation is increased in response to a determination at 1806 that the values of the patient parameters are below the specified range. In one embodiment, this includes performing the titration of the neurostimulation as discussed above (e.g., methods discussed with reference to FIGS. 12-15). Whether the current condition of the patient improves after the dose increase is determined by repeating the monitoring at 1804. At 1810, if the values of the patient parameters are not below the specified range, whether the values are above the specified range over the monitoring duration is determined. At 1812, the dose of the neurostimulation is decreased in response to a determination at 1810 that the values of the patient parameters are above the specified range. In one embodiment, this includes performing the titration of the neurostimulation as discussed above (e.g., methods discussed with reference to FIGS. 12-15). Whether the current condition of the patient improves after the dose decrease is determined by repeating the monitoring at 1804.

In one embodiment, steps 1804, 1806, 1808, 1810, and 1820 are repeated until the current condition of the patient improves such that the patient parameters become within the specified range. In one embodiment, system 100, including its various embodiments discussed in this document, is configured to perform method 1800. For example, stimulation control circuit 314 may be programmed to perform steps 1802, 1808, and 1812, and monitoring circuit 720 may be programmed to perform steps 1804, 1806, and 1810.

Figure 19:
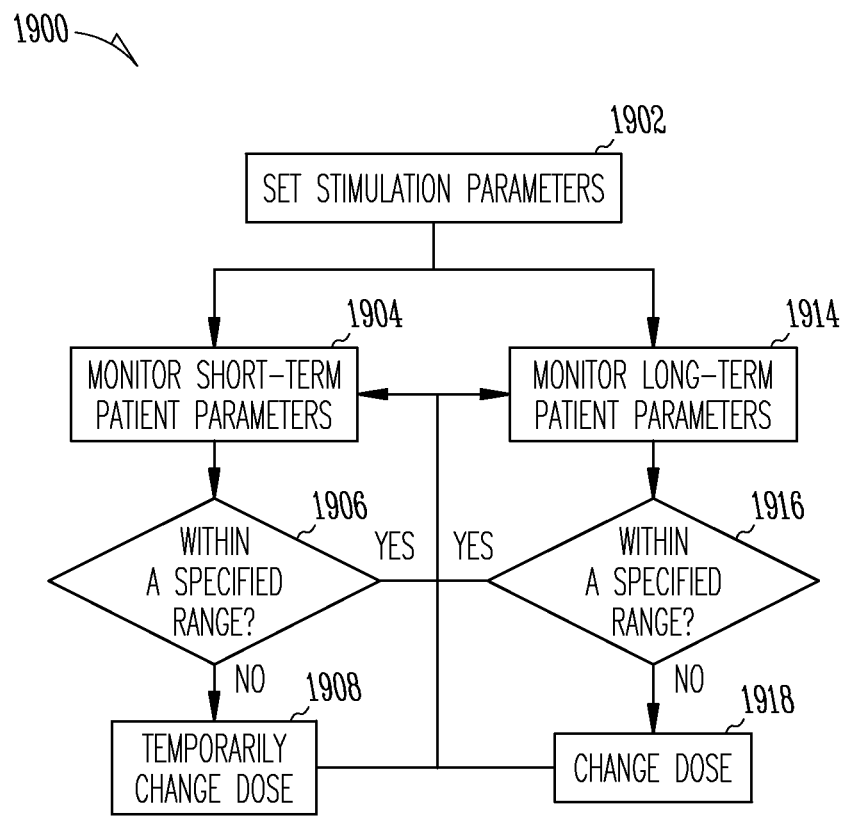
FIG. 19 is a flowchart illustrating an embodiment of a method for optimizing neurostimulation for short-term and long-term outcome.

FIG. 19 is a flowchart illustrating an embodiment of a method 1900 for optimizing neurostimulation for short-term and long-term outcome. The stimulation parameters used in method 1900 include the one or more sensor-driven parameters. Adjustment of the stimulation parameters includes adjustment of at least one of the one or more sensor driven parameters.

At 1902, the stimulation parameters are set. At 1904, short-term patient parameters are monitored. The short-term patient parameters are indicative of the current condition of the patient being an indication for short-term adjustment of the stimulation parameters. At 1906, whether the values of the short-term patient parameters are within a specified range (such as a target range) over a monitoring duration is determined. At 1908, the dose of the neurostimulation is temporarily changed in response to a determination at 1906 that the values of the short-term patient parameters are not within the specified range. In one embodiment, the stimulation parameters are approximately optimized such that the values of the short-term patient parameters are within the specified range. The one or more sensor-driven parameters are approximately optimized by performing the titration of the neurostimulation as discussed above (e.g., methods discussed with reference to FIGS. 12-15). In one embodiment, a temporary change in the dose of the neurostimulation is applied for a specified period of time after which the dose is reverted to its value before the change. Whether the current condition of the patient improves after the dose change is determined by repeating the monitoring at 1904. In one embodiment, steps 1904, 1906, and 1908 are repeated until the current condition of the patient improves such that the short-term patient parameters become within the specified range.

At 1914, long-term patient parameters are monitored. The long-term patient parameters are indicative of the current condition of the patient being an indication for permanent adjustment of the stimulation parameters. At 1916, whether the values of the long-term patient parameters are within a specified range (such as a target range) over a monitoring duration is determined. At 1918, the dose of the neurostimulation is changed in response to a determination at 1916 that the values of the long-term patient parameters are not within the specified range. In one embodiment, the stimulation parameters are approximately optimized such that the values of the long-term patient parameters are within the specified range. The one or more sensor-driven parameters are approximately optimized by performing the titration of the neurostimulation as discussed above (e.g., methods discussed with reference to FIGS. 12-15). Whether the current condition of the patient improves after the dose change is determined by repeating the monitoring at 1914. In one embodiment, steps 1914, 1916, and 1918 are repeated until the current condition of the patient improves such that the long-term patient parameters become within the specified range.

Steps 1904, 1906, and 1908 and steps 1914, 1916, and 1918 are performed concurrently to adjust the stimulation parameters in response to both short-term and long-term changes in the condition of the patient. In one embodiment, system 100, including its various embodiments discussed in this document, is configured to perform method 1900. For example, control circuit 314 may be programmed to perform steps 1902, 1908, and 1918, and monitoring circuit 720 may be programmed to perform steps 1904, 1906, 1914, and 1916.

Figure 20:
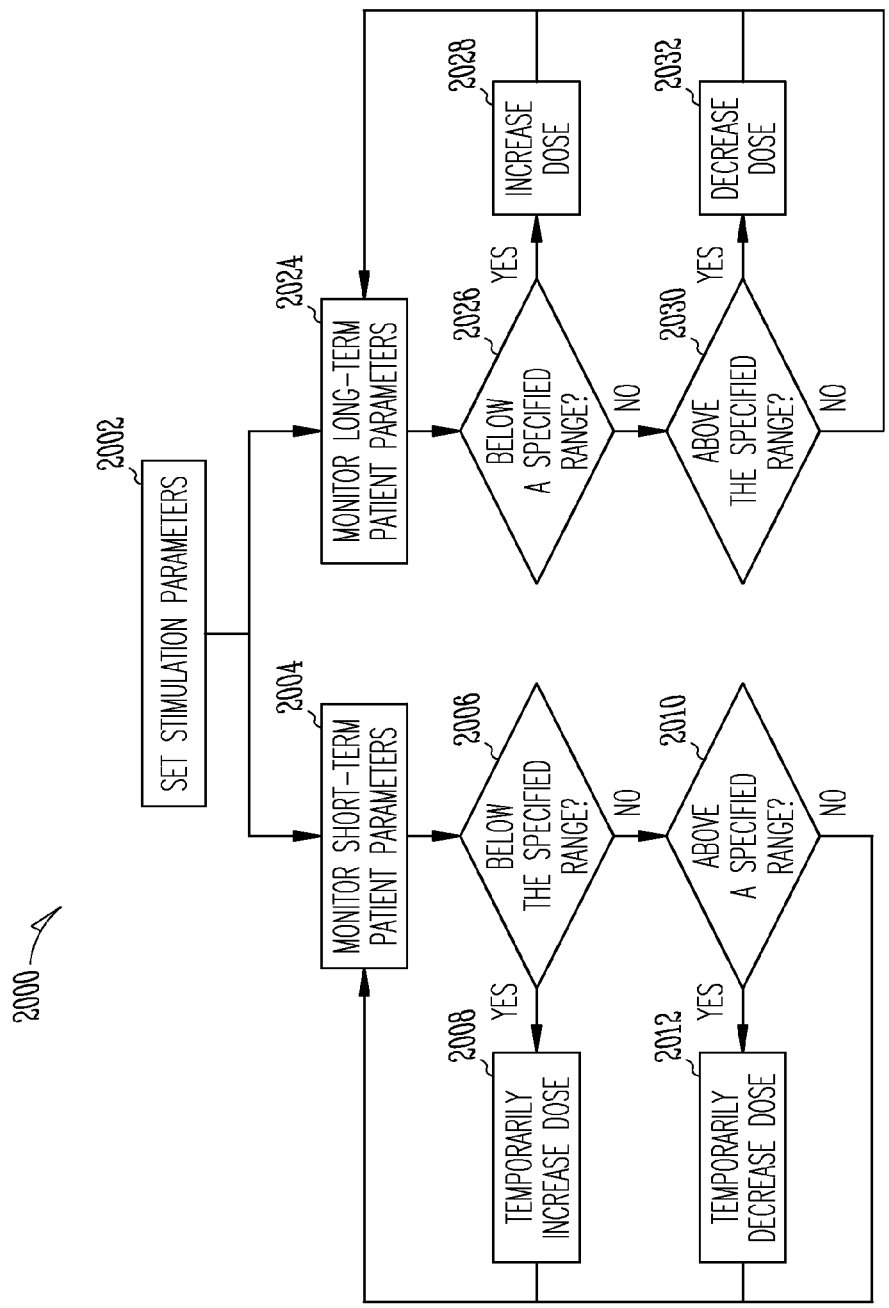
FIG. 20 is a flowchart illustrating another embodiment of the method for optimizing neurostimulation for short-term and long-term outcome.

FIG. 20 is a flowchart illustrating an embodiment of a method 2000 for optimizing neurostimulation for short-term and long-term outcome. Method 2000 is an embodiment of method 1900 and includes a further determination on whether the values of the patient parameters are each above or below its specified range.

At 2002, the stimulation parameters are set. At 2004, the short-term patient parameters are monitored. At 2006, whether the values of the short-term patient parameters are below the specified range over the monitoring duration is determined. At 2008, the dose of the neurostimulation is temporarily increased in response to a determination at 2006 that the values of the short-term patient parameters are below the specified range. In one embodiment, this includes performing the titration of the neurostimulation as discussed above (e.g., methods discussed with reference to FIGS. 12-15). In one embodiment, the stimulation parameters are approximately optimized such that the values of the short-term patient parameters are within the specified range. In one embodiment, a temporary increase in the dose of the neurostimulation is applied for a specified period of time after which the dose is decreased to its value before the increase. Whether the current condition of the patient improves after the dose increase is determined by repeating the monitoring at 2004. At 2010, if the values of the short-term patient parameters are not below the specified range, whether the values are above the specified range over the monitoring duration is determined. At 2012, the dose of the neurostimulation is temporarily decreased in response to a determination at 2010 that the values of the short-term patient parameters are above the specified range. In one embodiment, this includes performing the titration of the neurostimulation as discussed above (e.g., methods discussed with reference to FIGS. 12-15). Whether the current condition of the patient improves after the dose decrease is determined by repeating the monitoring at 2004. In one embodiment, a temporary decrease in the dose of the neurostimulation is applied for a specified period of time after which the dose is increased to its value before the decrease. In one embodiment, steps 2004, 2006, 2008, 2010, and 2012 are repeated until the current condition of the patient improves such that the short-term patient parameters become within the specified range.

At 2024, the long-term patient parameters are monitored. At 2026, whether the values of the long-term patient parameters are below the specified range over the monitoring duration is determined. At 2028, the dose of the neurostimulation is increased in response to a determination at 2026 that the values of the long-term patient parameters are below the specified range. In one embodiment, this includes performing the titration of the neurostimulation as discussed above (e.g., methods discussed with reference to FIGS. 12-15). In one embodiment, the stimulation parameters are approximately optimized such that the values of the long-term patient parameters are within the specified range. Whether the current condition of the patient improves after the dose increase is determined by repeating the monitoring at 2024. At 2030, if the values of the long-term patient parameters are not below the specified range, whether the values are above the specified range over the monitoring duration is determined. At 2032, the dose of the neurostimulation is decreased in response to a determination at 2030 that the values of the long-term patient parameters are above the specified range. In one embodiment, this includes performing the titration of the neurostimulation as discussed above (e.g., methods discussed with reference to FIGS. 12-15). Whether the current condition of the patient improves after the dose decrease is determined by repeating the monitoring at 2024. In one embodiment, steps 2024, 2026, 2028, 2030, and 2032 are repeated until the current condition of the patient improves such that the long-term patient parameters become within the specified range.

Steps 2004, 2006, 2008, 2010, and 2012 and steps 2024, 2026, 2028, 2030, and 2032 are performed concurrently to adjust the stimulation parameters in response to both short-term and long-term changes in the condition of the patient. In one embodiment, system 100, including its various embodiments discussed in this document, is configured to perform method 2000. For example, control circuit 314 may be programmed to perform steps 2002, 2008, 2012, 2028, and 2032, and monitoring circuit 720 may be programmed to perform steps 2004, 2006, 2010, 2024, 2026, and 2030.

Figure 21:
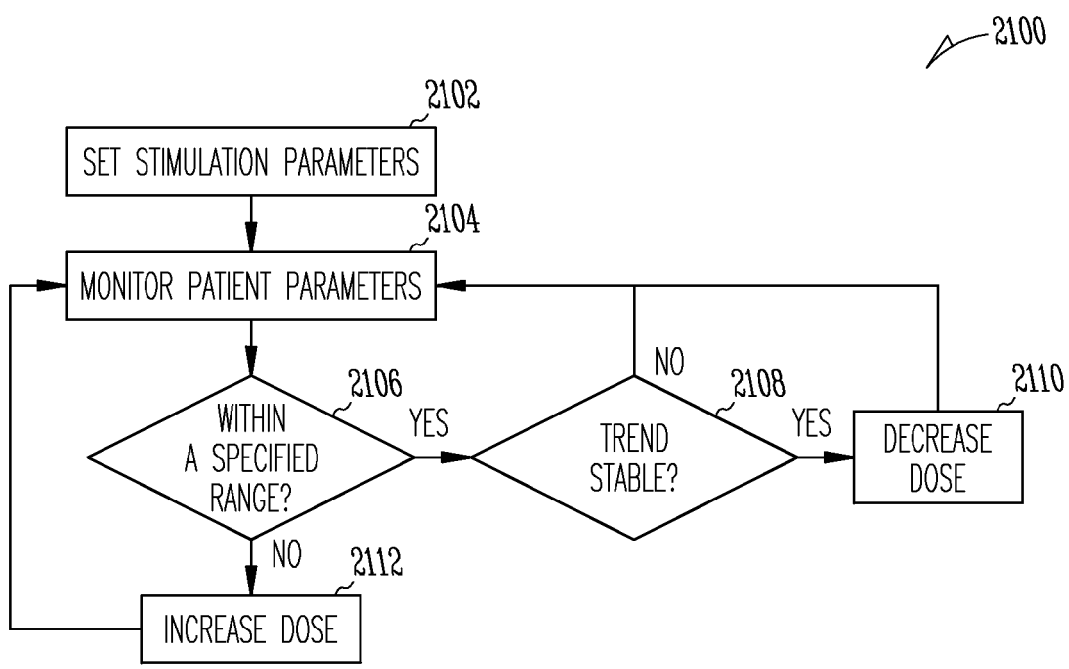
FIG. 21 is a flowchart illustrating an embodiment of a method for optimizing neurostimulation for battery longevity.

FIG. 21 is a flowchart illustrating an embodiment of a method 2100 for optimizing neurostimulation for battery longevity when the neurostimulation is delivered by an implantable medical device such as IMD 856 or 956. The stimulation parameters used in method 2100 include the one or more sensor-driven parameters. Adjustment of the stimulation parameters includes adjustment of at least one of the one or more sensor driven parameters. In various embodiments, method 2100 is performed to set the dose of the neurostimulation to an approximately optimal level above which additional dose does not further improve the condition of the patient.

At 2102, the stimulation parameters are set. In one embodiment, the initial values of the stimulation parameters are determined using acute titration methods such as by adjusting the stimulation parameters for desired level of laryngeal vibration and/or patient tolerance.

At 2104, patient parameters indicative of the current condition of the patient are monitored. The patient parameters are monitored by a chronic measurement (rather than an acute response to a change in therapy). Examples of the patient parameters to be monitored include heart rate variability (e.g., SDANN and LF/HF ratio), blood pressure (e.g., pulmonary artery pressure), activity, temperature, respiratory sinus arrhythmia ratio, spectral turbulence, and thoracic impedance. In one embodiment, one or more parameters each being a blend of multiple patient parameters are monitored. In one embodiment, the patient parameters to be monitored include measure of device efficacy such as percentage of biventricular pacing (in a combined pacing-neurostimulation device). In one embodiment, a rolling average for each of selected one or more patient parameter is monitored. The duration of averaging may be short-term (e.g., 5 minutes, 10 minutes, 1 hour, 4 hours, or 1 day) or long-term (e.g., 1 week or 1 month).

At 2106, whether the values of the patient parameters are within a specified range (such as a target range) over a monitoring duration is determined. The monitoring duration may be mid-term to long-term, such as 1 week to 1 month. At 2112, the dose of the neurostimulation is increased in response to a determination at 2106 that the values of the patient parameters are not within the specified range. In one embodiment, the stimulation parameters are approximately optimized such that the values of the patient parameters are within the specified range. The sensor-driven parameters are approximately optimized by performing the titration of the neurostimulation as discussed above (e.g., methods discussed with reference to FIGS. 12-15). Whether the current condition of the patient improves after the dose increase is determined by repeating the monitoring at 2104.

At 2108, whether one or more trends of the patient parameters are stable is determined in response to a determination at 2106 that the values of the patient parameters are within the specified range. At 2110, the dose of the neurostimulation is decreased in response to a determination at 2108 that the one or more trends are stable. Whether the current condition of the patient is degraded after the dose decrease is determined by repeating the monitoring at 2104. In one embodiment, subsequent to the decrease of the dose of the neurostimulation at 2110, in response to a determination that the values of the patient parameters are not within the specified range at 2106, the dose of the neurostimulation is reverted at 2112 to its value prior to the decrease at 2110.

If at least one of the one or more trends is determined to be unstable at 2108, the dose of the neurostimulation remains unchanged. In one embodiment, steps 2104, 2106, 2108, 2110, and 2112 are repeated to keep the patient parameters within the specified range while minimizing the dose of the neurostimulation to maximize the battery longevity.

In various embodiments, method 2100, including its various embodiments as discussed below, is performed to increase the battery longevity while maintaining an efficacious dose of the neurostimulation. In one embodiment, method 2100 is performed in response to a command issued by the user. In one embodiment, method 2100 is performed periodically to check whether the dose of the neurostimulation should be increased to improve the condition of the patient. In one embodiment, method 2100 is performed periodically to check whether the dose of the neurostimulation can be decreased while keeping the condition of the patient stable.

In one embodiment, system 100, including its various embodiments discussed in this document, is configured to perform method 2100. For example, stimulation control circuit 314 may be programmed to perform steps 2102, 2110, and 2112, and monitoring circuit 720 may be programmed to perform steps 2104, 2106, and 2108.

Figure 22:
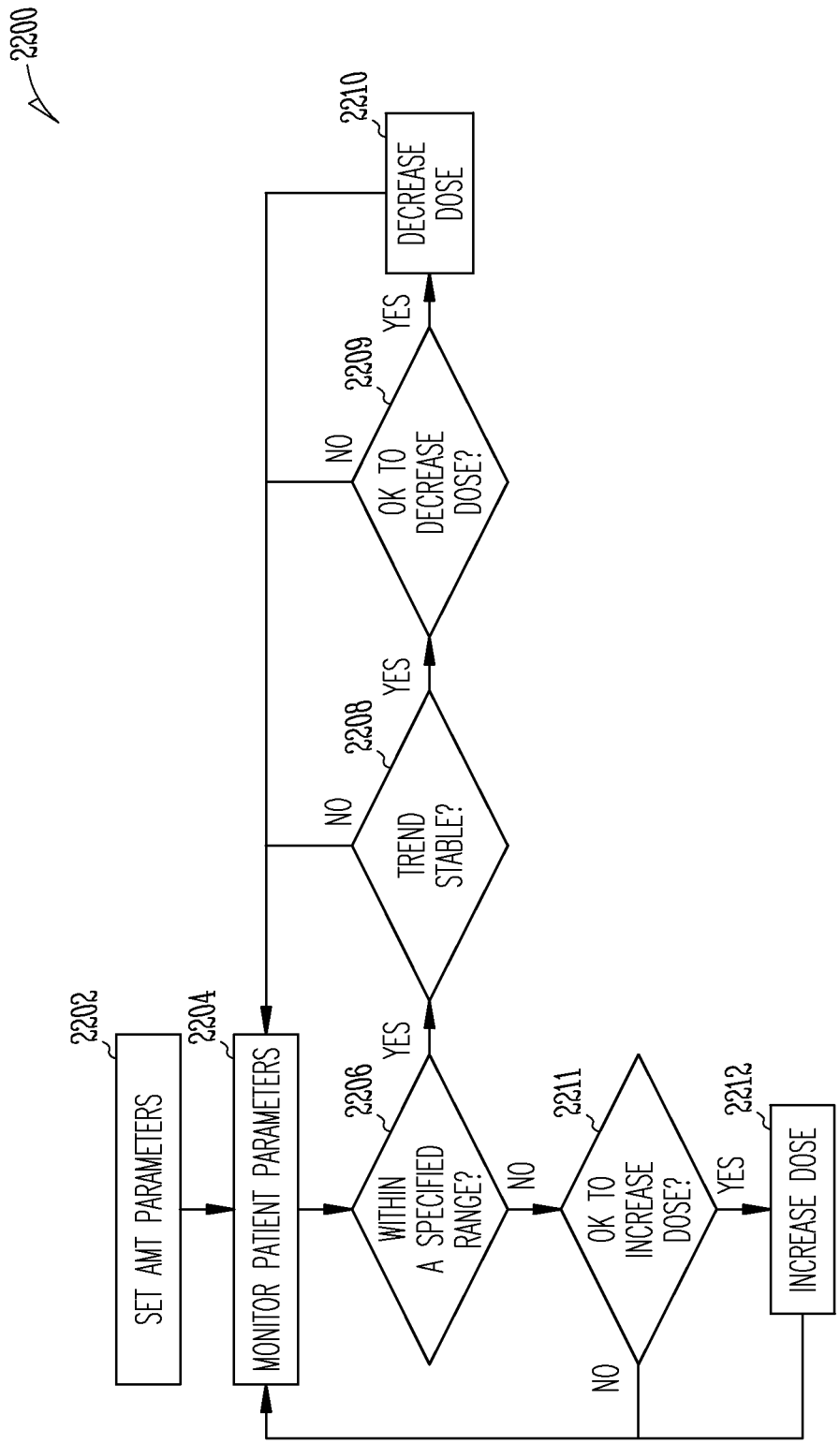
FIG. 22 is a flowchart illustrating another embodiment of the method for optimizing neurostimulation for battery longevity.

FIG. 22 is a flowchart illustrating an embodiment of a method 2200 for optimizing neurostimulation for battery longevity. Method 2200 is an embodiment of method 2200 and includes a further determination on whether the dose of the neurostimulation can be changed before the method calls for the change.

At 2202, the stimulation parameters are set. At 2204, patient parameters indicative of the current condition of the patient are monitored. At 2206, whether the values of the patient parameters are within a specified range (such as a target range) over the monitoring duration is determined. At 2211, whether the dose of the neurostimulation can be increased is determined in response to a determination at 2206 that the values of the patient parameters are not within the specified range. In various embodiments, examples for inhibiting an increase in the dose of the neurostimulation include that the increase in the dose is associated with degradation of the condition of the patient in the past, that the dose is already at its maximum level provided by the device delivering the neurostimulation, and that a specified maximum number of dose increase or dose change over a specified time period has already been reached. At 2212, the dose of the neurostimulation is increased in response to a determination at 2211 that it may be increased. Whether the current condition of the patient improves after the dose increase is determined by repeating the monitoring at 2204.

At 2208, whether one or more trends of the patient parameters are stable is determined in response to a determination at 2206 that the values of the patient parameters are within the specified range. At 2209, whether the dose of the neurostimulation can be decreased is determined in response to a determination at 2208 that the one or more trends are stable. In various embodiments, examples for inhibiting a decrease in the dose of the neurostimulation include that the decrease in the dose is associated with degradation of the condition of the patient in the past, that the dose is already at its minimum level provided by the device delivering the neurostimulation, and that a specified maximum number of dose decrease or dose change over a specified time period has already been reached. At 2210, the dose of the neurostimulation is decreased in response to a determination at 2209 that it can be decreased. Whether the current condition of the patient is degraded after the dose decrease is determined by repeating the monitoring at 2204. In one embodiment, subsequent to the decrease in the dose of the neurostimulation at 2210, in response to a determination that the values of the patient parameters are not within the specified range at 2206, the dose of the neurostimulation is reverted at 2212 to its value prior to the decrease at 2210.

If at least one of the one or more trends is determined to be unstable at 2208, the dose of the neurostimulation remains unchanged. In one embodiment, steps 2204, 2206, 2208, 2209, 2210, 2211, and 2212 are repeated to keep the patient parameters within the specified range while minimizing the dose of the neurostimulation to maximize the battery longevity.

In one embodiment, system 100, including its various embodiments discussed in this document, is configured to perform method 2200. For example, stimulation control circuit 314 may be programmed to perform steps 2202, 2209, 2210, 2211, and 2112, and monitoring circuit 720 may be programmed to perform steps 2204, 2206, and 2208.

Figure 23:
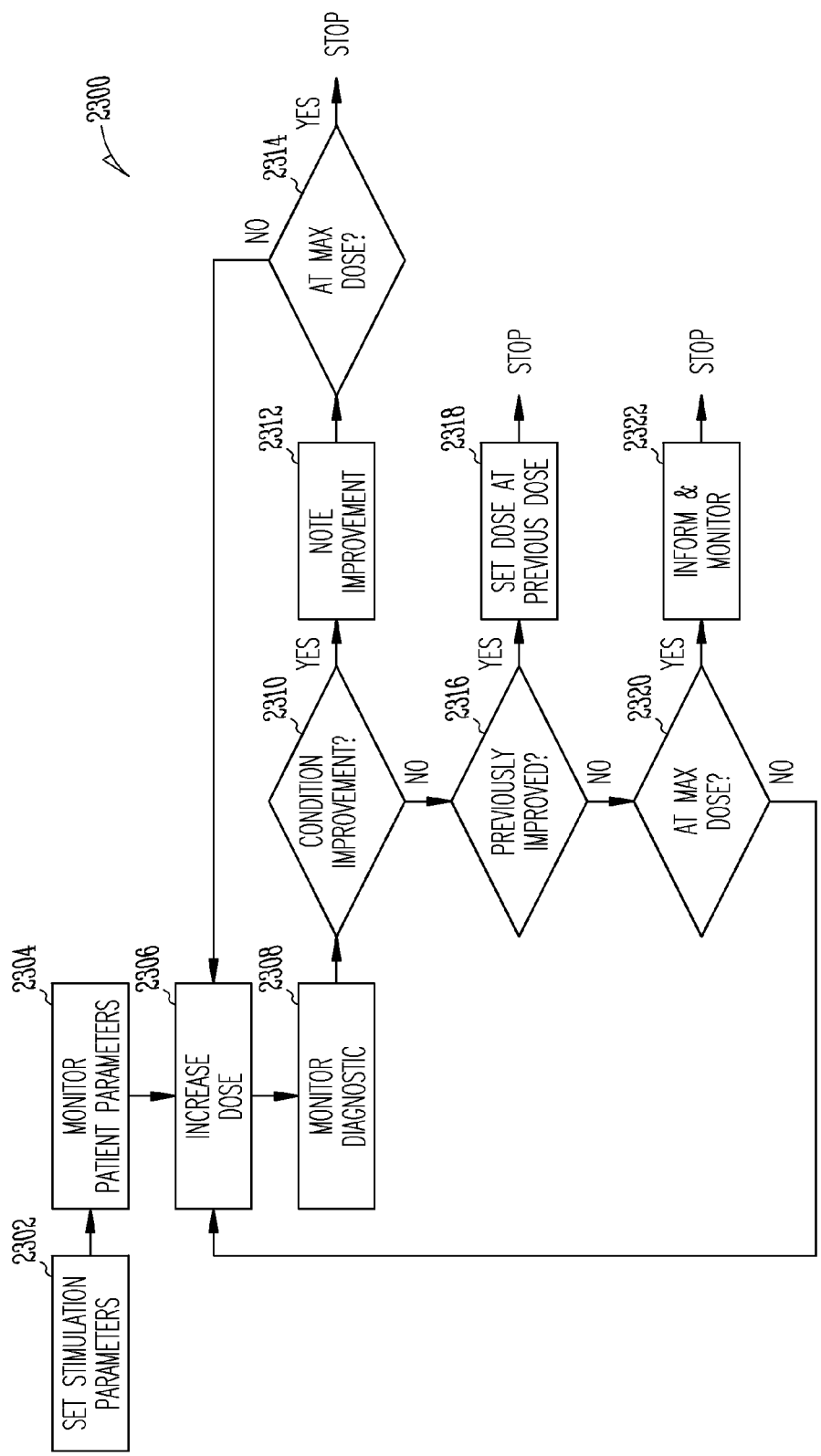
FIG. 23 is a flowchart illustrating another embodiment of the method for optimizing neurostimulation for battery longevity.

FIG. 23 is a flowchart illustrating an embodiment of a method 2300 for optimizing neurostimulation for battery longevity when the neurostimulation is delivered by an implantable medical device such as IMD 856 or 956. The stimulation parameters used in method 2300 include the one or more sensor-driven parameters. Adjustment of the stimulation parameters includes adjustment of at least one of the one or more sensor driven parameters. In various embodiments, method 2300 is performed to set the dose of the neurostimulation to an approximately optimal level above which additional dose does not further improve the condition of the patient.

At 2302, the stimulation parameters are set. In one embodiment, the initial values of the stimulation parameters are determined using acute titration methods such as by adjusting the stimulation parameters for desired level of laryngeal vibration and/or patient tolerance.

At 2304, patient parameters indicative of the current condition of the patient are monitored. The patient parameters are monitored by a chronic measurement (rather than an acute response to a change in therapy). Examples of the patient parameters to be monitored include heart rate variability (e.g., SDANN and LF/HF ratio), blood pressure (e.g., pulmonary artery pressure), activity, temperature, respiratory sinus arrhythmia ratio, spectral turbulence, and thoracic impedance. In one embodiment, one or more parameters each being a blend of multiple patient parameters are monitored. In one embodiment, the patient parameters to be monitored include measure of device efficacy such as percentage of biventricular pacing (in a combined pacing-neurostimulation device). In one embodiment, a rolling average for each of selected one or more patient parameter is monitored. The duration of averaging may be short-term (e.g., 5 minutes, 10 minutes, 1 hour, 4 hours, or 1 day) or long-term (e.g., 1 week or 1 month).

At 2306, the dose of the neurostimulation is increased. At 2308, the patient parameters are monitored for result of increase in the dose of neurostimulation.

At 2310, whether the increase in the dose of neurostimulation at 2306 improves the condition of the patient is determined. At 2312, a note that the dose resulting from the increase at 2306 results in the improvement of the condition of the patient is made. At 2314, whether the dose of the neurostimulation is already at its maximum level available from the device delivering the neurostimulation is determined. In response to a determination that the dose of the neurostimulation is not already at its maximum level, the dose of the neurostimulation is further increased at 2306. In response to a determination at 2314 that the dose of the neurostimulation is already at its maximum level, the performance of method 2300 is concluded.

At 2316, whether the last increase in the dose of neurostimulation at 2306 improved the condition of the patient is determined in response to a determination at 2310 that the current increase in the dose of neurostimulation at 2306 does not improve the condition of the patient. At 2318, the dose of the neurostimulation is reverted to its value prior to the current increase at 2306, and the performance of method 2300 is concluded.

At 2320, whether the dose of the neurostimulation is already at its maximum level available from the device delivering the neurostimulation is determined in response to a determination at 2316 that the last increase in the dose of neurostimulation at 2306 did not improve the condition of the patient. At 2322, the user is informed, and the patient parameters are continued to be monitored, in response to a determination at 2320 that the dose of the neurostimulation is already at its maximum level, and the performance of method 2300 is concluded. In response to a determination at 2320 that the dose of the neurostimulation is not already at its maximum level, the dose of the neurostimulation is further increased at 2306.

In one embodiment, system 100, including its various embodiments discussed in this document, is configured to perform method 2300. For example, stimulation control circuit 314 may be programmed to perform steps 2302, 2306, 2312, 2314, 2318, 2320, and 2322, and monitoring circuit 720 may be programmed to perform steps 2306, 2308, 2310, and 2316.

Figure 24:
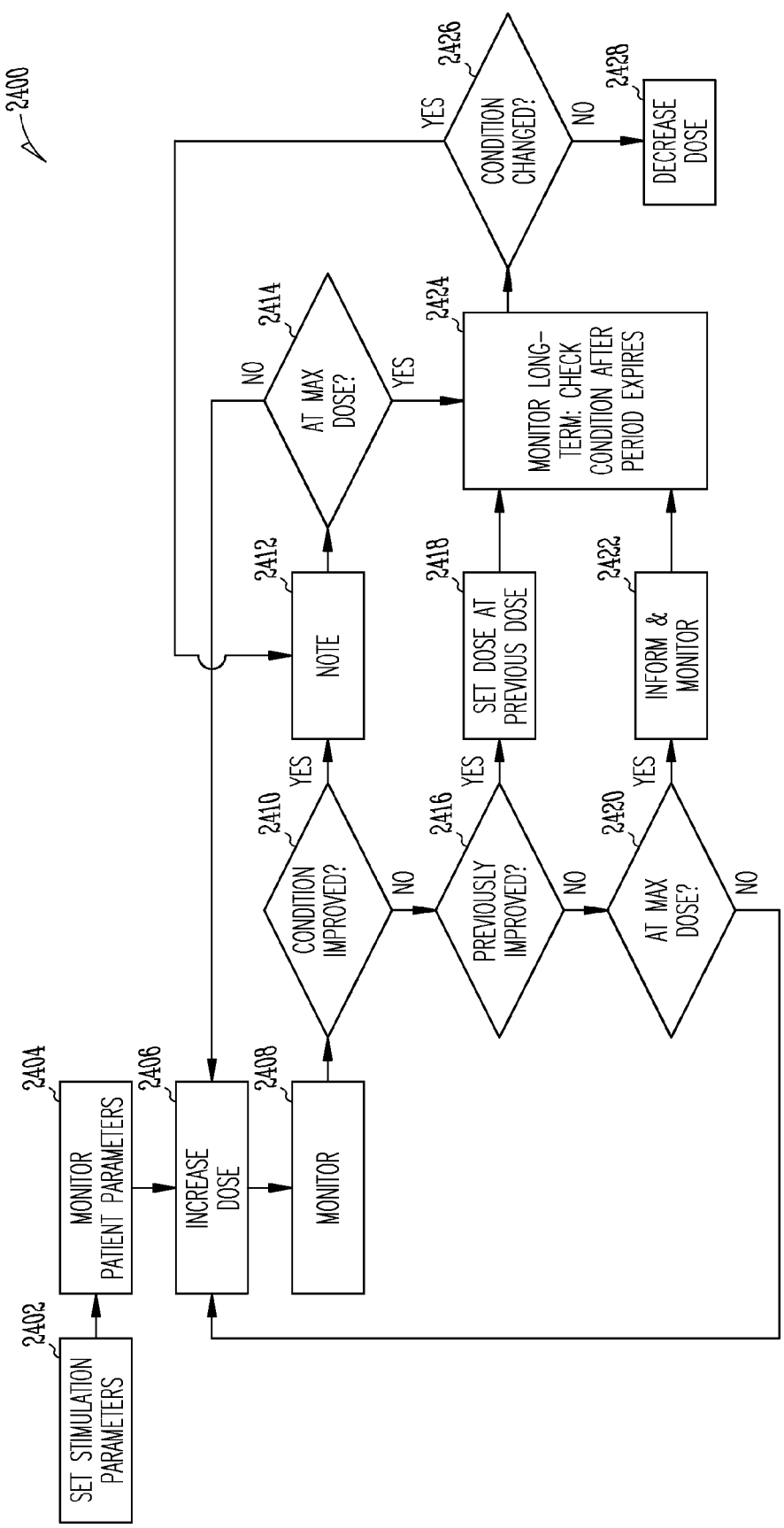
FIG. 24 is a flowchart illustrating another embodiment of the method for optimizing neurostimulation for battery longevity.

FIG. 24 is a flowchart illustrating an embodiment of a method 2400 for optimizing neurostimulation for battery longevity. Method 2400 is an embodiment of method 2300 and further includes continued monitoring of the condition of the patient after a performance of method 2300 is concluded.

At 2402, the stimulation parameters are set. At 2304, the patient parameters are monitored. At 2306, the dose of the neurostimulation is increased. At 2308, the patient parameters are monitored for result of the increase in the dose of neurostimulation.

At 2410, whether the increase in the dose of neurostimulation at 2406 improves the condition of the patient is determined. At 2412, a note that the dose resulting from the increase at 2406 results in the improvement of the condition of the patient is made. At 2414, whether the dose of the neurostimulation is already at its maximum level available from the device delivering the neurostimulation is determined. In response to a determination at 2414 that the dose of the neurostimulation is not already at its maximum level, the dose of the neurostimulation is further increased at 2406. In response to a determination that the dose of the neurostimulation is already at its maximum level, the condition of the patient is continued to be monitored at 2424.

At 2416, whether the last increase in the dose of neurostimulation at 2406 improved the condition of the patient is determined in response to a determination at 2410 that the current increase in the dose of neurostimulation at 2406 does not improve the condition of the patient. At 2418, the dose of the neurostimulation is reverted to its value prior to the current increase at 2406, and the condition of the patient is continued to be monitored at 2424.

At 2420, whether the dose of the neurostimulation is already at its maximum level available from the device delivering the neurostimulation is determined in response to a determination at 2416 that the last increase in the dose of neurostimulation at 2406 did not improve the condition of the patient. At 2422, the user is informed in response to a determination that the dose of the neurostimulation is already at its maximum level, and the condition of the patient is continued to be monitored at 2424. In response to a determination at 2414 that the dose of the neurostimulation is not already at its maximum level, the dose of the neurostimulation is further increased at 2406.

At 2426, whether the condition of the patient is changed is determined. In response to a determination at 2426 that the condition of the patient is changed, a note is made to record the change at 2412. At 2428, the dose of the neurostimulation is decreased in response to a determination at 2426 that the condition of the patient is not changed, and then the patient is continued to be monitored at 2424.

In one embodiment, system 100, including its various embodiments discussed in this document, is configured to perform method 2400. For example, stimulation control circuit 314 may be programmed to perform steps 2402, 2406, 2412, 2414, 2418, 2420, 2422, and 2428, and monitoring circuit 720 may be programmed to perform steps 2406, 2408, 2410, 2416, 2424, and 2428.

Figure 25:
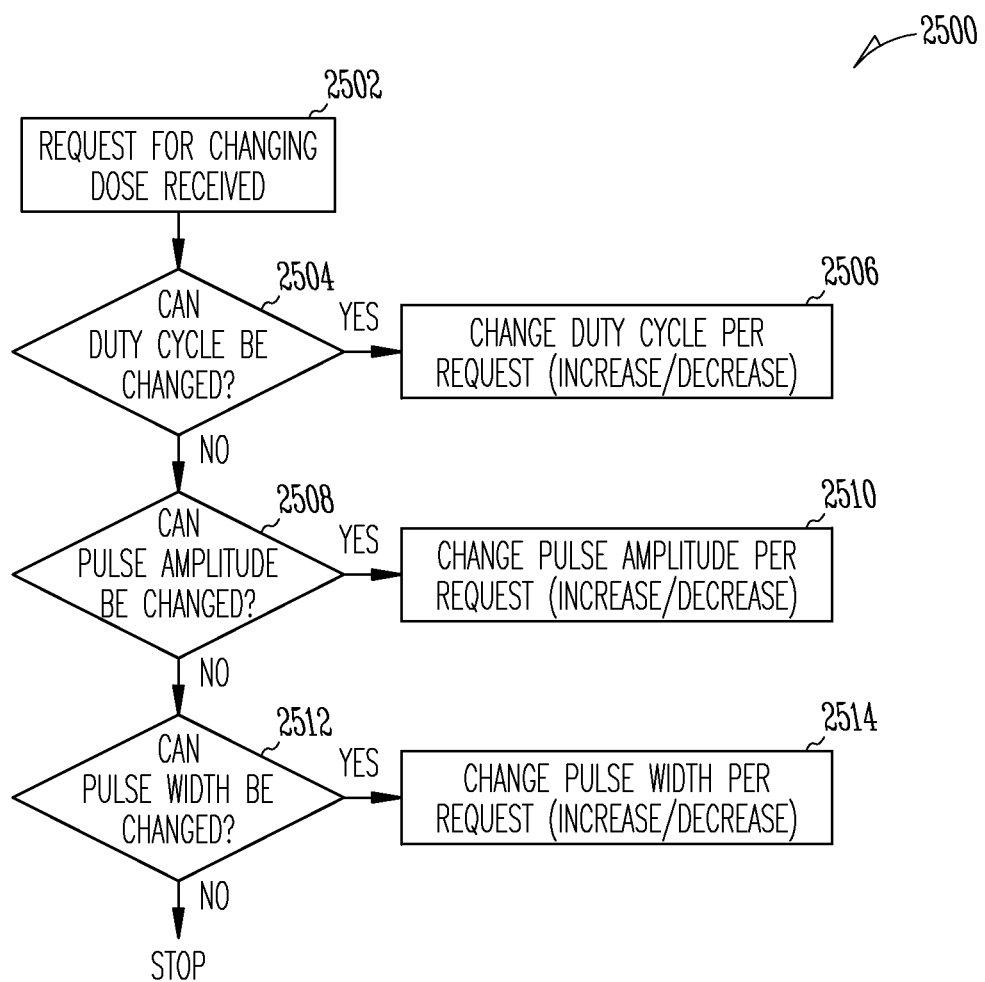
FIG. 25 is a flowchart illustrating an embodiment of a method for adjusting dosing during titration of neurostimulation.

FIG. 25 is a flowchart illustrating an embodiment of a method 2500 for adjusting dosing during titration of neurostimulation. In the illustrated embodiment, the sensor-driven parameters to be adjusted during the titration of the neurostimulation includes duty cycle, pulse amplitude, and pulse width. In various embodiments, method 2500 is applied during performance of any methods of titration of neurostimulation discussed in this document.

At 2502, a request for changing dosing is received. In various embodiments, the request is made during the titration of the neurostimulation when another set of values of the sensor-driven parameters is to be tested. At 2504, whether the duty cycle can be changed is determined. In one embodiment, the duty cycle is the ratio of on-time (time period during which the neurostimulation pulses are delivered) to off-time (time period during which the neurostimulation pulses are not delivered) specified in percentage. In another embodiment, the duty cycle is specified as the on-time given a specified unit cycle. At 2506, the duty cycle is changed (increased or decreased) in response to the request if it is determined at 2504 that the duty cycle can be changed. At 2508, whether the pulse amplitude can be changed is determined if it is determined at 2504 that the duty cycle cannot be changed. The pulse amplitude is the amplitude of the stimulation pulse specified as a voltage or a current. At 2510, the pulse amplitude is changed (increased or decreased) in response to the request if it is determined at 2508 that the pulse amplitude can be changed. At 2512, whether the pulse width can be changed is determined if it is determined at 2508 that the pulse amplitude cannot be changed. The pulse width is the width of each stimulation pulse. At 2514, the pulse amplitude is changed (increased or decreased) in response to the request if it is determined at 2512 that the pulse width can be changed.

In various embodiments, examples of reasons for which a sensor-driven parameter cannot be changed as determined (for example, at 2504, 2508, or 2512) include that the requested change would result in a value of the parameter associated with degradation of the condition of the patient in the past, that the current value of the parameter is already at its maximum or minimum level provided by the device delivering the neurostimulation, and that a specified maximum number of change in the parameter over a specified time period has already been reached.

Increase in amount of charge delivered with the neurostimulation pulses is known to increase nerve fiber recruitment (amount of nerve fibers captured), which translates to greater efficacy for the neurostimulation. Increase of the duty cycle, the pulse amplitude, and the pulse width each increase the amount of charge delivered. The order of the change of the sensor-driven parameters in the illustrated embodiment is recommended under the assumption that a prior titration (such as an initial titration) has already set the most tolerable pulse amplitude, and increase in the duty cycle does not affect the patient's tolerability of the pulse amplitude.

In one embodiment, system 100, including its various embodiments discussed in this document, is configured to perform method 2500. For example, stimulation parameter adjustor 318 may be programmed to perform method 2500.

Figure 26:
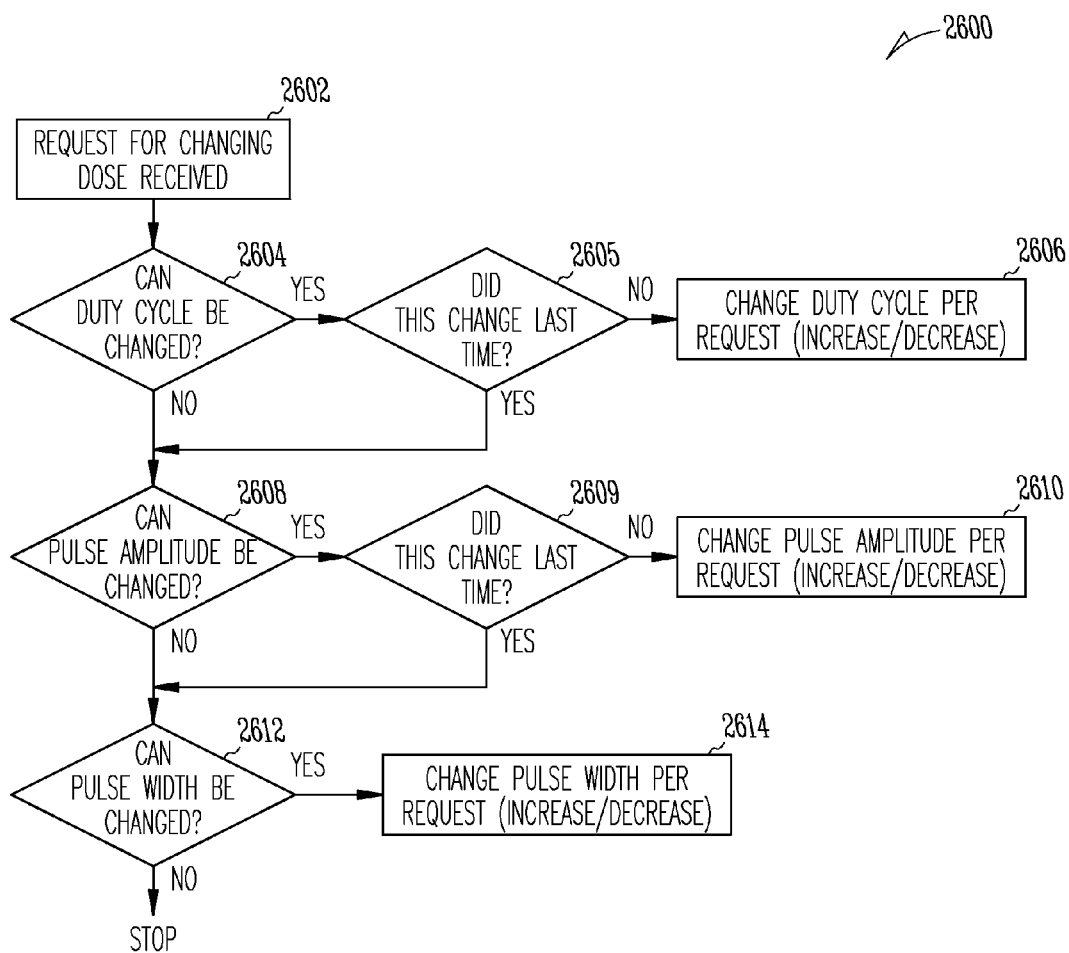
FIG. 26 is a flowchart illustrating another embodiment of the method for adjusting dosing during titration of neurostimulation.

FIG. 26 is a flowchart illustrating an embodiment of a method 2600 for adjusting dosing during titration of neurostimulation. Method 2600 is an embodiment of method 2500 in which the sensor-driven parameter to be changed in response to a current request is different from the sensor-driven parameter changed in response to the last request.

At 2602, a request for changing dose is received. At 2604, whether the duty cycle can be changed is determined. At 2605, whether the duty cycle was changed in response to the last request for change dose is determined if it is determined at 2604 that the duty cycle can be changed. At 2606, the duty cycle is changed (increased or decreased) in response to the request if it is determined at 2605 that the duty cycle was not changed in response to the last request for changing dose. At 2608, whether the pulse amplitude can be changed is determined if it is determined at 2604 that the duty cycle cannot be changed or if it is determined at 2605 that the duty cycle was changed in response to the last request for changing dose. At 2609, whether the pulse amplitude was changed in response to the last request for changing dose is determined if it is determined at 2608 that the pulse amplitude can be changed. At 2610, the pulse amplitude is changed (increased or decreased) in response to the request if it is determined at 2609 that the duty cycle was not changed in response to the last request for changing dose. At 2612, whether the pulse width can be changed is determined if it is determined at 2608 that the pulse amplitude cannot be changed or if it is determined at 2609 that the pulse amplitude was changed in response to the last request for changing dose. At 2614, the pulse width is changed (increased or decreased) in response to the request if it is determined at 2612 that the pulse width can be changed.

In one embodiment, system 100, including its various embodiments discussed in this document, is configured to perform method 2600. For example, stimulation parameter adjustor 318 may be programmed to perform method 2600.

Figure 27:
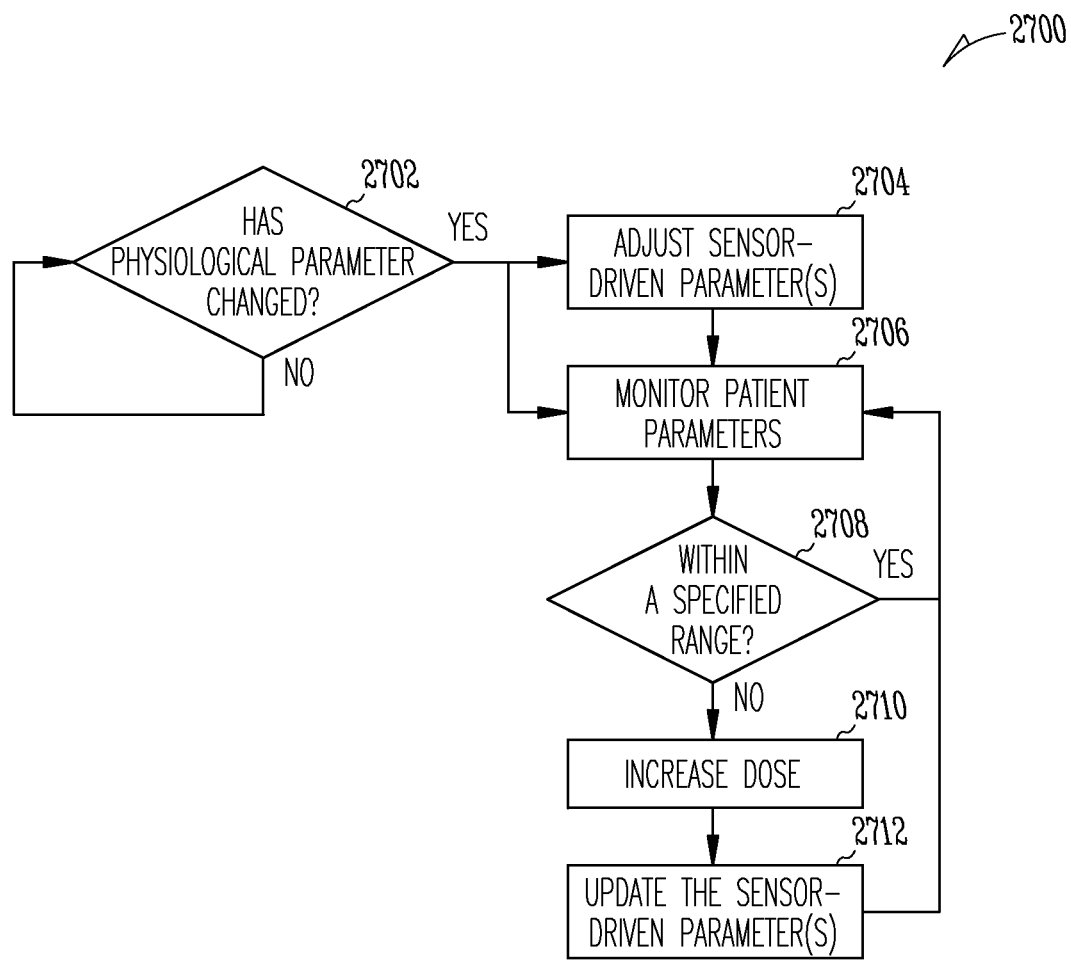
FIG. 27 is a flowchart illustrating an embodiment of a method for optimizing neurostimulation using one or more physiological parameters.

FIG. 27 is a flowchart illustrating an embodiment of a method 2700 for optimizing neurostimulation using one or more physiological parameters. In various embodiments, such one or more physiological parameters are known to affect autonomic activity and/or balance. In various embodiments, the one or more sensor-driven parameters are adjusted for the one or more physiological parameters.

At 2702, a change in the value of a physiological parameter is being detected. Examples of the physiological parameter includes the patient's posture, activity level, temperature, or a parameter being a function of any one or more of the posture, activity level, and temperature. In various embodiments, the physiological parameter includes any parameter indicative of a physical or physiological condition of the patient that is known to affect autonomic function of the patient. At 2704, one or more sensor-dependent values of the one or more sensor-driven parameters are adjusted in response to a detection of change in the value of the physiological parameter. At 2706, patient parameters indicative of the current condition of the patient are monitored. Examples of the patient parameters to be monitored include heart rate, heart rate variability (e.g., SDANN and LF/HF ratio), blood pressure (e.g., pulmonary artery pressure), activity, temperature, respiratory sinus arrhythmia ratio, spectral turbulence, and thoracic impedance. In one embodiment, one or more parameters each being a blend of multiple patient parameters are monitored.

At 2708, whether the values of the patient parameters are within a specified range (such as a target range) over a monitoring duration is determined. At 2710, the dose of the neurostimulation is increased in response to a determination at 2708 that the values of the patient parameters are not within the specified range. At 2712, the sensor-dependent values for the sensor-driven parameters are updated for the current value (after the detection of the change in the value of the sensor parameter) of the sensor parameter.

In one embodiment, system 100, including its various embodiments discussed in this document, is configured to perform method 2700. For example, stimulation control circuit 314 may be programmed to perform steps 2704, 2710, and 2712, and monitoring circuit 720 may be programmed to perform steps 2702, 2706, and 2708.

Figure 28:
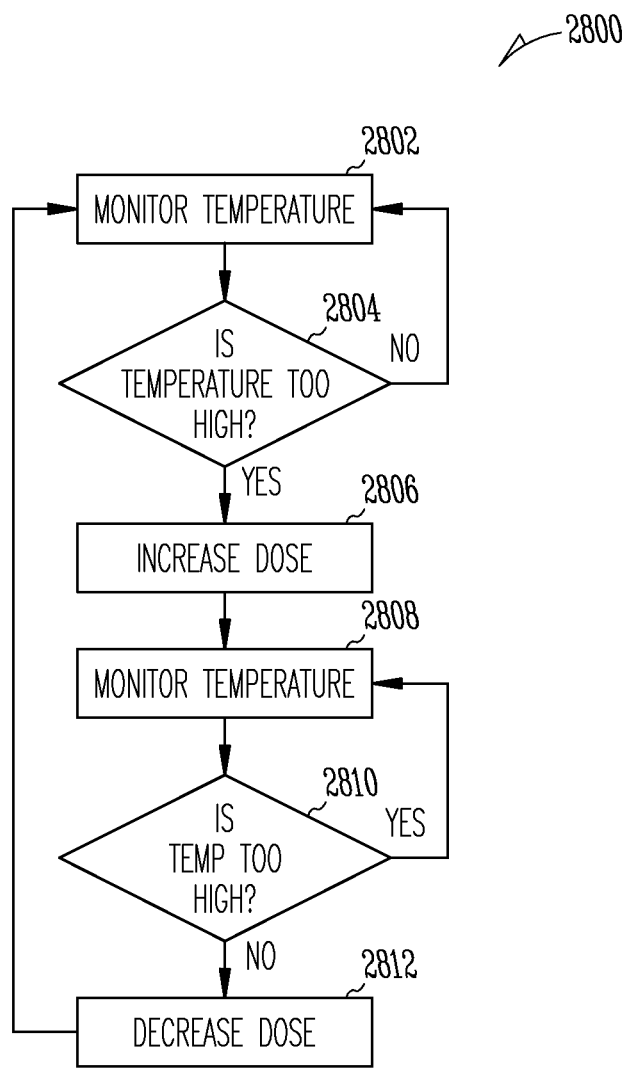
FIG. 28 is a flowchart illustrating an embodiment of a method for optimizing neurostimulation using temperature.

FIG. 28 is a flowchart illustrating an embodiment of a method 2800 for optimizing neurostimulation using temperature. Method 2800 is an embodiment of method 2700 with the one or more physiological parameters including the temperature of the patient. An increase in temperature indicates an inflammatory response for which the dose of the neurostimulation is to be increased.

At 2802, the temperature of the patient is monitored. At 2804, whether the temperature is too high (exceeds a threshold temperature, for example) is determined. At 2806, the dose of the neurostimulation is increased in response to a determination at 2804 that the temperature is too high. At 2808, the temperature after the increase in the dose of the neurostimulation is monitored. At 2810, whether the temperature is too high (exceeds a threshold temperature, for example) is determined. At 2812, the dose of the neurostimulation is decreased in response to a determination at 2810 that the temperature is not too high.

In one embodiment, system 100, including its various embodiments discussed in this document, is configured to perform method 2800. For example, stimulation control circuit 314 may be programmed to perform steps 2806 and 2812, and monitoring circuit 720 may be programmed to perform steps 2802, 2804, 2808, and 2810.

Figure 29:
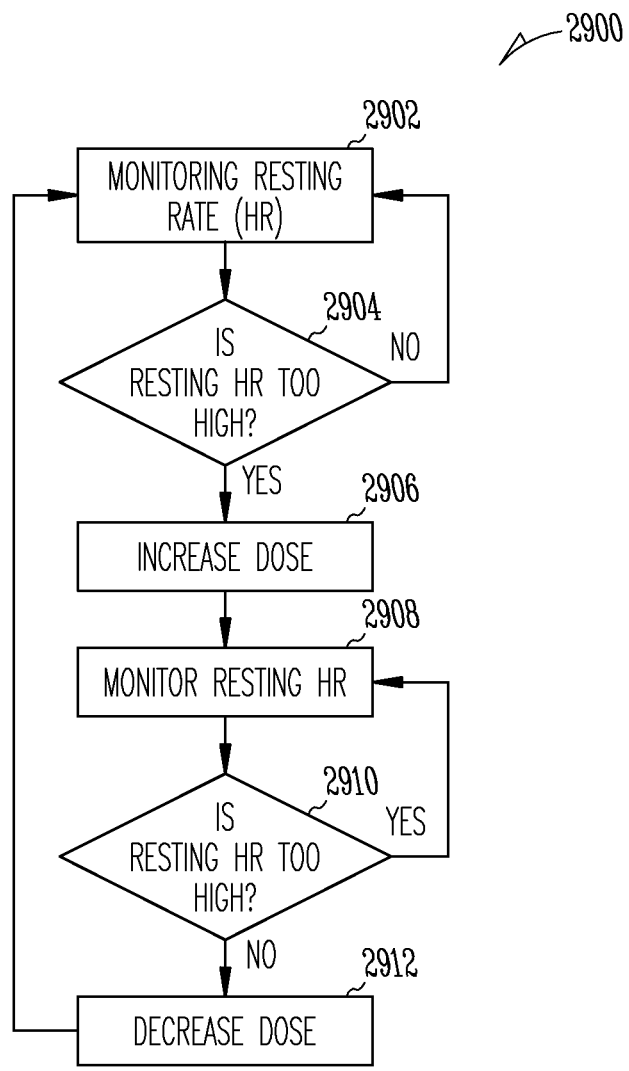
FIG. 29 is a flowchart illustrating an embodiment of a method for optimizing neurostimulation using heart rate.

FIG. 29 is a flowchart illustrating an embodiment of a method for optimizing neurostimulation using resting heart rate. Method 2900 is an embodiment of method 2700 with the one or more physiological parameters including the resting heart rate of the patient (i.e., the heart rate of the patient at rest at rest). A high resting heart rate indicates excessive sympathetic activity for which the dose of the neurostimulation (such as vagus nerve stimulation) is to be increased.

At 2902, the resting heart rate of the patient is monitored. At 2904, whether the resting heart rate is too high (exceeds a threshold heart rate, for example) is determined. At 2906, the dose of the neurostimulation is increased in response to a determination at 2904 that the resting heart rate is too high. At 2908, the resting heart rate after the increase in the dose of the neurostimulation is monitored. At 2910, whether the resting heart rate is too high (exceeds a threshold heart rate, for example) is determined. At 2912, the dose of the neurostimulation is decreased in response to a determination at 2910 that the resting heart rate is not too high.

In one embodiment, the increase in the dose of the neurostimulation at 2906 includes an increase in the duty cycle of the neurostimulation. In another embodiment, a ratio of the duty cycle to the resting heart rate is set such that the duty cycle increases in response to the increase in the resting heart rate, and decreases in response to the decrease in the resting heart rate. If the set ratio cannot lower the resting heart rate to a normal value (below the threshold heart rate, for example), the ratio of the duty cycle to the resting heart rate is to be increased.

In one embodiment, system 100, including its various embodiments discussed in this document, is configured to perform method 2900. For example, stimulation control circuit 314 may be programmed to perform steps 2906 and 2912, and monitoring circuit 720 may be programmed to perform steps 2902, 2904, 2908, and 2910.

Figure 30:
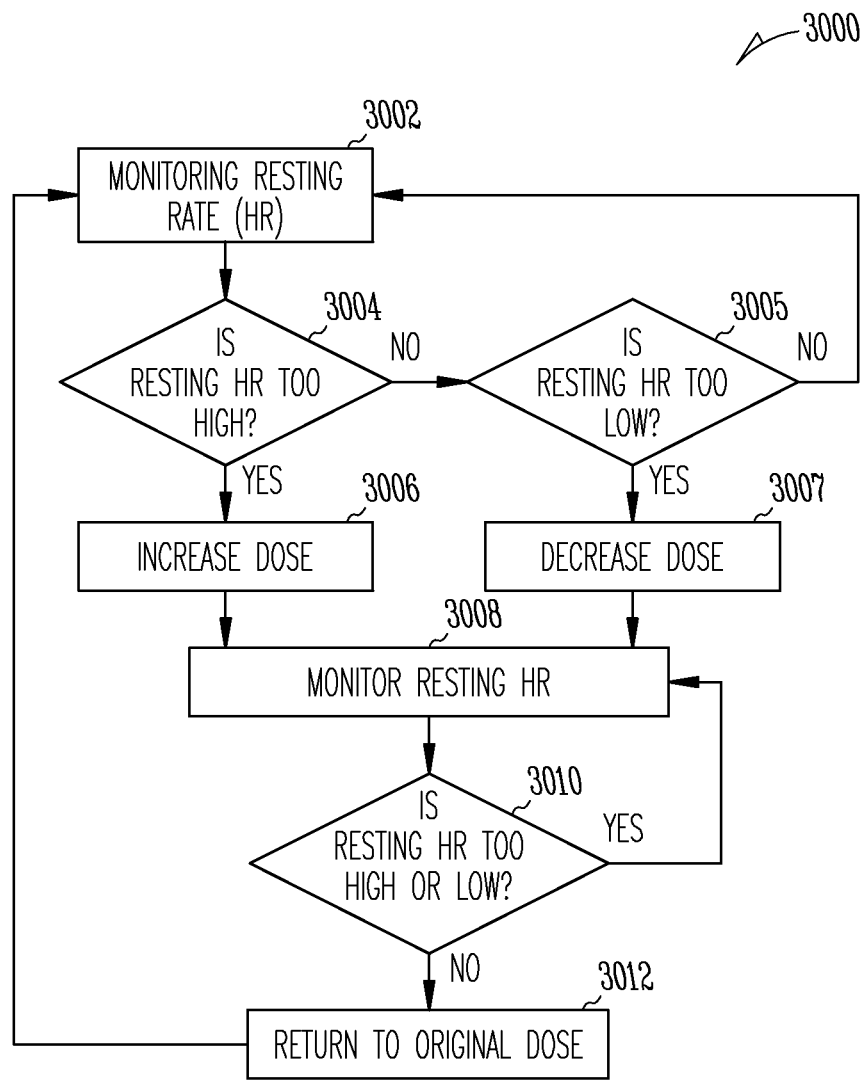
FIG. 30 is a flowchart illustrating another embodiment of a method for optimizing neurostimulation using heart rate.

FIG. 30 is a flowchart illustrating an embodiment of a method 3000 for optimizing neurostimulation using resting heart rate. Method 3000 is an embodiment of method 2900 providing for returning the dose of the neurostimulation in response to the resting heart rate returning to its normal range.

At 3002, the resting heart rate of the patient is monitored. At 3004, whether the resting heart rate is too high (exceeds a first threshold heart rate, for example) is determined. At 3006, the dose of the neurostimulation is increased in response to a determination at 3004 that the resting heart rate is too high. At 3005, concurrently with 3004, whether the resting heart rate is too low (below a second threshold heart rate, for example) is determined. At 3007, the dose of the neurostimulation is decreased in response to a determination at 3005 that the resting heart rate is too low.

At 3008, the resting heart rate after the increase or decrease in the dose of the neurostimulation is monitored. At 3010, whether the resting heart rate is too high (exceeds the first threshold heart rate, for example) or too low (below the second threshold heart rate, for example) is determined. At 3012, the dose of the neurostimulation is reset to its value before the increase at 3006 or decrease at 3007 in response to a determination at 3010 that the resting heart rate is neither too high nor too low.

In one embodiment, system 100, including its various embodiments discussed in this document, is configured to perform method 3000. For example, stimulation control circuit 314 may be programmed to perform steps 3006, 3007, and 3012, and monitoring circuit 720 may be programmed to perform steps 3002, 3004, 3005, 3008, and 3010.

Figure 31:
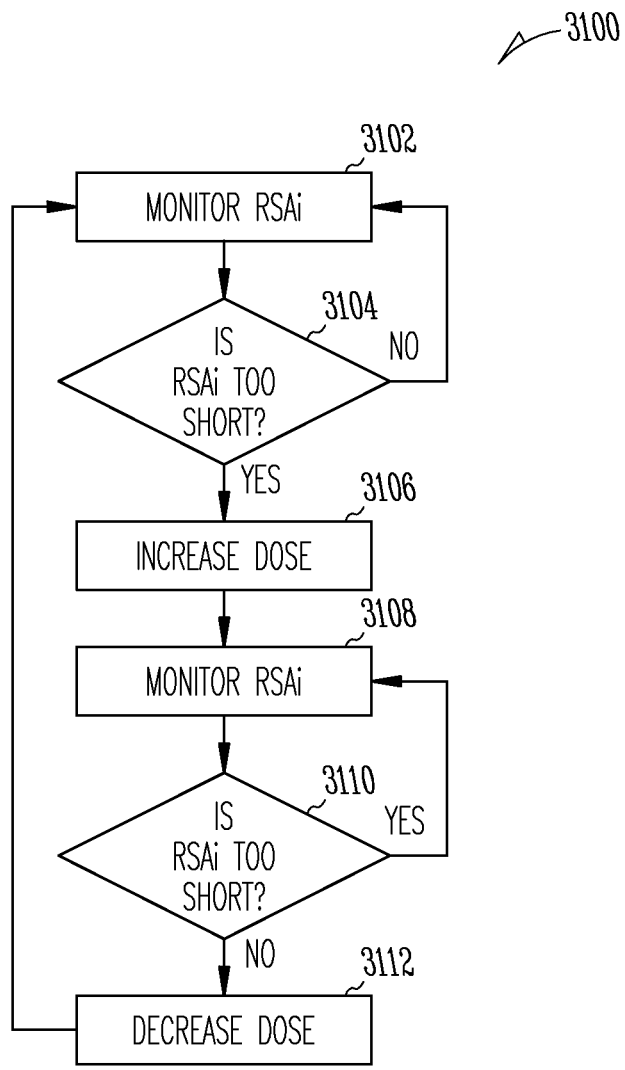
FIG. 31 is a flowchart illustrating an embodiment of a method for optimizing neurostimulation using respiratory sinus arrhythmia interval (RSAi).

FIG. 31 is a flowchart illustrating an embodiment of a method 3100 for optimizing neurostimulation using respiratory sinus arrhythmia interval (RSAi). Method 3000 is an embodiment of method 2700 with the one or more physiological parameters including the RSAi of the patient. An abnormally short RSAi indicates insufficient parasympathetic activity for which the dose of the neurostimulation (such as vagus nerve stimulation) is to be increased.

At 3102, the RSAi of the patient is monitored. In one embodiment, the monitored RASi is the RASi during expiration when the patient is at rest. At 3104, whether the RSAi is too short (less than a threshold interval, for example) is determined. At 3106, the dose of the neurostimulation is increased in response to a determination at 3104 that the temperature is too high. At 3108, the RSAi after the increase in the dose of the neurostimulation is monitored. At 3110, whether the RSAi is too short (less than a threshold interval, for example) is determined. At 3112, the dose of the neurostimulation is decreased in response to a determination at 3110 that the RSAi is not too short.

In one embodiment, system 100, including its various embodiments discussed in this document, is configured to perform method 3100. For example, stimulation control circuit 314 may be programmed to perform steps 3106 and 3112, and monitoring circuit 720 may be programmed to perform steps 3102, 3104, 3108, and 3110.

Various embodiments discussed in this document provide for titration of neurostimulation for short-term and long-term efficacy as well as battery longevity of an implantable neurostimulator. In various embodiments, patient parameters indicative of current condition of the patient are monitored as functions of a sensor parameter that indicates the patient's physical state such as posture and/or activity level. For example, the patient parameters are each monitored for each of predefined values of the sensor parameter such as erect, erect with activity, prone, supine, left lateral supine, right lateral supine, sitting, and on or immediately after transitions between states. One or more sensor-driven parameters controlling the neurostimulation are approximately optimized for a posture and/or activity level when the values of the patient parameters for that posture and/or activity level are not within a specified range. In various embodiments, such one or more sensor-driven parameters determine dose level of the neurostimulation for the patient. In various embodiments, the titration of the neurostimulation provides for dose levels associated with each value of the sensor parameter such that the dose level for the patient is adjusted in response to a change in the sensor parameter. In various embodiments, a limit is imposed on the number of times the one or more sensor-driven parameters can be adjusted in response to a change in the value of the sensor parameter. In various embodiments, the one or more sensor-driven parameters are adjusted in response to the values of the monitored patient parameters being outside a specified range for at least a specified minimum duration. In various embodiments, the patient parameters are trended, and the extent of each adjustment of the one or more sensor-driven parameters are recorded, as factors determining how the one or more sensor-driven parameters will be adjusted in the future. In various embodiments, the titration of the neurostimulation is performed on an ambulatory basis when opportunities are present. Such opportunities include the presence of the patient's physical state or condition for which the neurostimulation is titrated, and have lengths depending on the nature of opportunities. For example, the patient standing for 4 hours may provide for a short term opportunity, a week-ling illness may provide for a medium-term opportunity, and change in a drug therapy 11 weeks prior to a scheduled titration of the neurostimulation may provide for a moderately long-term opportunity.

It is to be understood that the above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A system for delivering neurostimulation to a patient, the system comprising:
   a sensor circuit configured to determine a current value of a sensor parameter representing a physical state of the patient;
   a stimulation output circuit configured to deliver the neurostimulation; and
   a stimulation control circuit configured to store a plurality of values of a sensor-driven parameter, identify a value of the sensor-driven parameter for the current value of the sensor parameter from the stored plurality of values of the sensor-driven parameter, determine whether the identified value of the sensor-driven parameter is currently optimal, control the delivery of the neurostimulation using the identified value of the sensor-driven parameter in response to the identified value of the sensor-driven parameter being determined to be currently optimal, and perform a titration of the neurostimulation for the current value of the sensor parameter in response to the identified value of the sensor-driven parameter being determined to be currently not optimal.

2. The system of claim 1, wherein the sensor circuit comprises:
   a posture sensor configured to sense a posture signal indicative of a posture of the patient; and
   a sensor processing circuit configured to determine the current value of the sensor parameter using the sensed posture signal.

3. The system of claim 1, wherein the sensor circuit comprises:
   an activity sensor configured to sense an activity signal indicative of an activity level of the patient; and
   a sensor processing circuit configured to determine the current value of the sensor parameter using the sensed activity signal.

4. The system of claim 1, comprising a parameter input device configured to receive the plurality of values of the sensor-driven parameter front a user.

5. The system of claim 1, wherein the stimulation control circuit is configured to determine whether the identified value of the sensor-driven parameter is currently optimal based on whether the neurostimulation was the titrated for the current value of the sensor parameter within a specified period of time.

6. The system of claim 1, comprising a monitoring circuit configured to monitor one or more physiological signals indicative of one or more effects of the neurostimulation, and wherein the stimulation control circuit is configured to perform the titration of the neurostimulation using the one or more physiological signals.

7. The system of claim 6, wherein the monitoring circuit comprises an intended effect monitor configured to produce one or more intended effect parameters each indicative of a degree of an intended effect caused by the neurostimulation using the one or more physiological signals, and the stimulation control circuit is configured to approximately optimize the value of the sensor-driven parameter for the current value of the sensor parameter using the one or more intended effect parameters.

8. The system of claim 6, wherein the monitoring circuit comprises a side effect monitor configured to produce one or more side effect parameters each indicative of a degree of a side effect caused by the neurostimulation using the one or more physiological signals, and the stimulation control circuit is configured to approximately optimize the value of the sensor-driven parameter for the current value of the sensor parameter using the one or more side effect parameters.

9. A system for delivering neurostimulation to a patient, the system comprising:
a sensor circuit configured to determine a current value of a sensor parameter representing a physical state of the patient;
a stimulation output circuit configured to deliver the neurostimulation; and
a stimulation control circuit configured to store a plurality of values of a sensor-driven parameter, identify a value of the sensor-driven parameter for the current value of the sensor parameter from the stored plurality of values of the sensor-driven parameter, determine whether the identified value of the sensor-driven parameter is currently optimal, control the delivery of the neurostimulation using the identified value of the sensor-driven parameter in response to the identified value of the sensor-driven parameter being determined to be currently optimal, and approximately optimize the plurality of values of the sensor-driven parameter by performing a titration of the neurostimulation for a corresponding plurality of values of the sensor parameter.

10. The system of claim 9, wherein the sensor circuit comprises:
a posture sensor configured to sense a posture signal indicative of a posture of the patient; and
a sensor processing circuit configured to determine the current value of the sensor parameter using the sensed posture signal.

11. The system of claim 9, wherein the sensor circuit comprises:
an activity sensor configured to sense an activity signal indicative of an activity level of the patient; and
a sensor processing circuit configured to determine the current value of the sensor parameter using the sensed activity signal.

12. A method for controlling neurostimulation, the method comprising:
storing a plurality of values of a sensor-driven parameter;
delivering neurostimulation to a patient;
determining a current value of a sensor parameter indicative of a physical state of the patient;
identifying a value of the sensor-driven parameter for the current value of the sensor parameter from the stored plurality of values of the sensor-driven parameter;
determining whether the identified value of the sensor parameter is currently optimal;
controlling the delivery of the neurostimulation using the identified value of the sensor-driven parameter in response to the identified value of the sensor-driven parameter being determined to be currently optimal; and
titrating the neurostimulation for the current value of the sensor parameter in response to the identified value of the sensor-driven parameter being determined to be currently not optimal.

13. The method of claim 12, wherein titrating the neurostimulation comprises:
monitoring a degree of a side effect of the neurostimulation; and
approximately optimizing the identified value of the sensor-driven parameter based on the degree of the side effect of the neurostimulation.

14. The method of claim 13, wherein titrating the neurostimulation comprises:
monitoring one or more physiological signals;
producing one or more side effect parameters each indicative of the degree of the side effect of the neurostimulation using the one or more physiological signals;
producing one or more trends of the one or more side effect parameters; and
approximately optimizing the identified value of the sensor-driven parameter using the one or more trends of the one or more side effect parameters.

15. The method of claim 12, wherein titrating the neurostimulation comprises:
monitoring a degree of an intended effect of the neurostimulation; and
approximately optimizing the identified value of the sensor-driven parameter based on the degree of the intended effect of the neurostimulation.

16. The method of claim 15, wherein titrating the neurostimulation comprises:
monitoring one or more physiological signals;
producing one or more intended effect parameters each indicative of the degree of the intended effect of the neurostimulation using the one or more physiological signals;
producing one or more trends of the one or more intended effect parameters; and
approximately optimizing the identified value of the sensor-driven parameter using the one or more trends of the one or more intended effect parameters.

17. The method of claim 12, wherein delivering the neurostimulation comprises delivering the neurostimulation from an implantable medical device, and titrating the neurostimulation comprises automatically titrating the neurostimulation using a control circuit of the implantable medical device programmed to titrate the neurostimulation.

18. The method of claim 17, wherein determining the current value of the sensor parameter comprises:
sensing a posture signal indicative of a posture of the patient; and
determining the current value of the sensor parameter using the posture signal.

19. The method of claim 17, wherein determining the current value of the sensor parameter comprises:
sensing an activity signal indicative of an activity level of the patient; and
determining the current value of the sensor parameter using the activity signal.

20. The method of claim 17, comprising approximately optimizing the plurality of values of the sensor-driven parameter by automatically titrating the neurostimulation for a corresponding plurality of values of the sensor parameter.

* * * * *